(12) United States Patent
Alvarez et al.

(10) Patent No.: US 10,610,625 B2
(45) Date of Patent: Apr. 7, 2020

(54) HYDRAULIC PUMPING SYSTEM FOR EXPRESSION OF BREAST MILK

(71) Applicant: ExploraMed NC7, Inc., Mountain View, CA (US)

(72) Inventors: Jeffery B. Alvarez, Redwood City, CA (US); Leo Centeno, East Palo Alto, CA (US); William Tolmasoff, Oakland, CA (US); Brett Swope, Gaithersburg, MD (US); Alex Forman, San Francisco, CA (US); Kyung R. Park, Fremont, CA (US)

(73) Assignee: ExploraMed NC7, Inc., Mountain View, CA (US)

( * ) Notice: Subject to any disclaimer, the term of this patent is extended or adjusted under 35 U.S.C. 154(b) by 136 days.

(21) Appl. No.: 15/581,973

(22) Filed: Apr. 28, 2017

(65) Prior Publication Data
US 2017/0312409 A1 Nov. 2, 2017

Related U.S. Application Data

(60) Provisional application No. 62/329,917, filed on Apr. 29, 2016.

(51) Int. Cl.
*A61M 1/06* (2006.01)
*A61M 1/00* (2006.01)
(Continued)

(52) U.S. Cl.
CPC .......... *A61M 1/062* (2014.02); *A61M 1/0072* (2014.02); *A61M 1/06* (2013.01);
(Continued)

(58) Field of Classification Search
CPC ........ A61M 1/06; A61M 1/062; A61M 1/064; A61M 1/066; A61M 1/0037;
(Continued)

(56) References Cited

U.S. PATENT DOCUMENTS 2,275,477 A * 3/1942 Sundholm ............... F16K 3/085
251/149.8
4,161,307 A * 7/1979 Clinch ..................... B60H 1/00
251/193

(Continued)

OTHER PUBLICATIONS

International Search Report dated Jul. 13, 2017 for International Application No. PCT/US2017/030155.

*Primary Examiner* — Scott J Medway

(57) ABSTRACT

A hydraulic pumping system in accordance with embodiments comprises a breast interface operably coupled to an actuatable assembly by means of an actuatable assembly interface. The breast interface comprises a distal membrane coupled to a housing to form a fluid reservoir therebetween. The actuatable assembly interface comprises a proximal membrane. The distal and proximal membranes are fluidly coupled via a tube carrying a driving fluid. The actuatable assembly interface is configured to removably couple to the actuatable assembly, in order to operably couple the actuatable assembly to the breast interface. The actuatable assembly interface comprises a fluid shut off mechanism to reversibly shut off fluid communication between the breast interface and the actuatable assembly interface when the actuatable assembly interface is decoupled from the actuatable assembly.

15 Claims, 16 Drawing Sheets

(51) Int. Cl.
*F04B 43/067* (2006.01)
*F04B 23/02* (2006.01)
*F04B 43/00* (2006.01)
*F04B 43/06* (2006.01)
*F04B 53/06* (2006.01)

(52) U.S. Cl.
CPC .......... *F04B 23/02* (2013.01); *F04B 43/0081* (2013.01); *F04B 43/06* (2013.01); *F04B 43/067* (2013.01); *F04B 53/06* (2013.01)

(58) Field of Classification Search
CPC .............. A61M 1/0072; A61M 1/0031; A61M 16/0057; F01L 1/34; F01L 1/348; F01L 7/02; F01L 7/023; F01L 7/06; F01L 7/16; F16K 11/074; F16K 3/085; F16K 3/32; Y10T 137/5109; Y10T 137/86823
See application file for complete search history.

(56) References Cited

U.S. PATENT DOCUMENTS

| | | | |
|---|---|---|---|
| 5,071,403 A | 12/1991 | Larsson | |
| 5,215,450 A * | 6/1993 | Tamari | A61M 1/0031 138/119 |
| 5,295,957 A | 3/1994 | Aida et al. | |
| 5,308,040 A | 5/1994 | Torres | |
| 5,358,476 A * | 10/1994 | Wilson | A61M 1/06 604/74 |
| 5,814,004 A * | 9/1998 | Tamari | A61M 1/0031 251/10 |
| 6,039,078 A * | 3/2000 | Tamari | A61M 1/0031 138/30 |
| 6,290,671 B1 | 9/2001 | Niederberger | |
| 7,093,818 B2 * | 8/2006 | Koeneman | F16K 11/074 251/207 |
| 7,316,384 B2 * | 1/2008 | Sekiya | F16K 11/0743 251/129.11 |
| 7,526,911 B2 * | 5/2009 | Pickard | F02C 9/263 60/39.281 |
| 7,766,866 B2 | 8/2010 | Nuesch et al. | |
| 9,616,156 B2 | 4/2017 | Alvarez et al. | |
| 9,623,160 B2 * | 4/2017 | Alvarez | A61M 1/062 |
| 2013/0267892 A1 * | 10/2013 | Woolford | A61M 3/0258 604/34 |
| 2014/0163488 A1 * | 6/2014 | Vaillancourt | F16B 2/22 604/319 |
| 2015/0018784 A1 * | 1/2015 | Coulthard | A61M 1/0035 604/319 |
| 2016/0000982 A1 | 1/2016 | Alvarez et al. | |

* cited by examiner

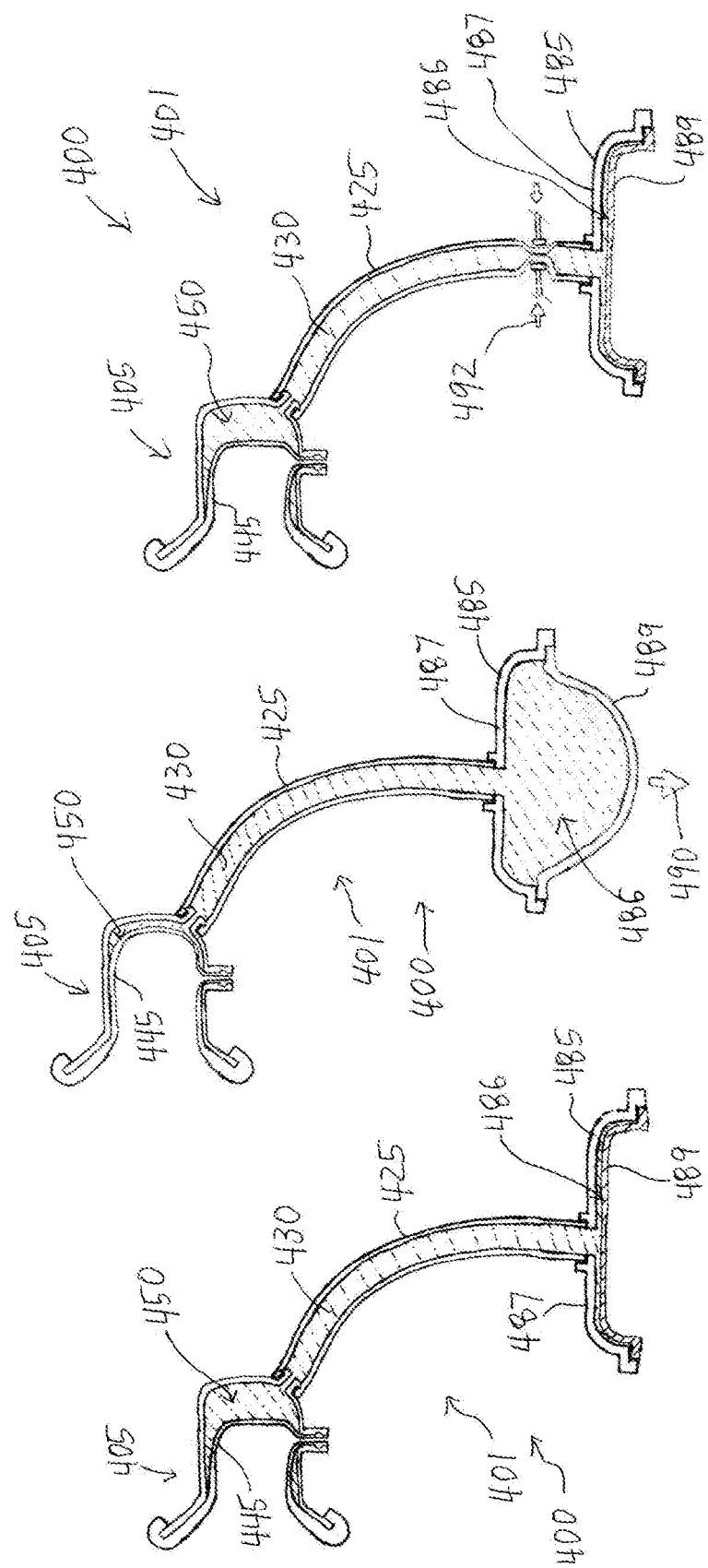

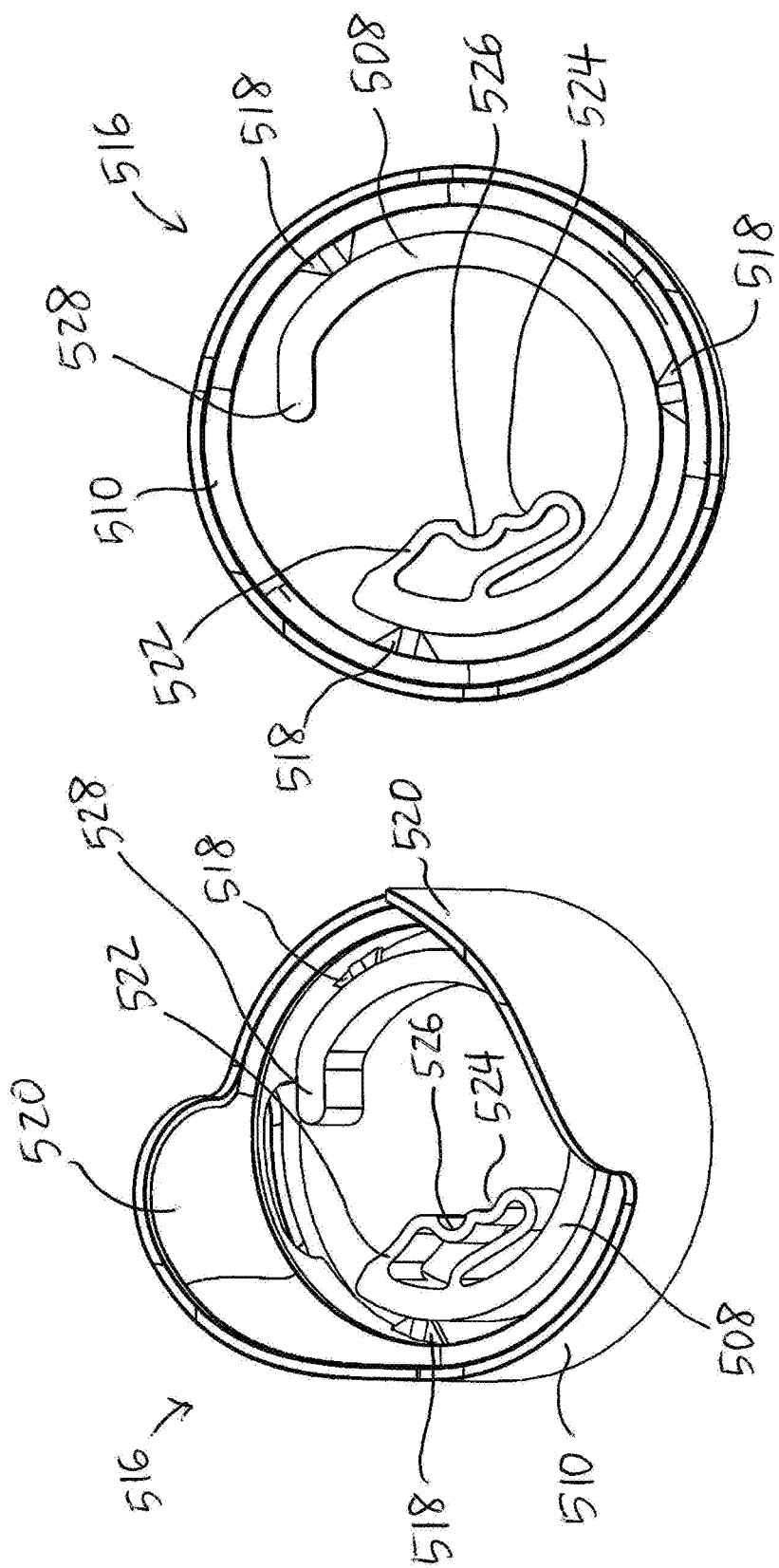

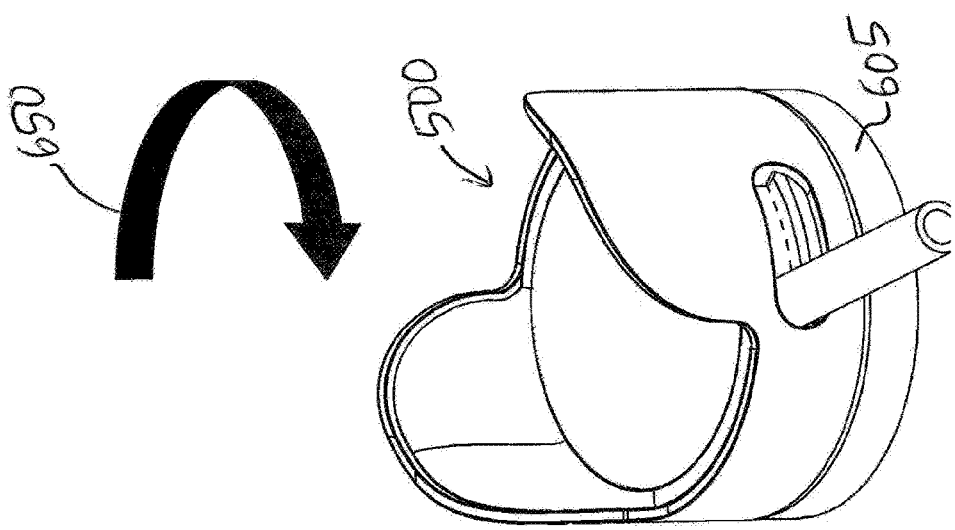
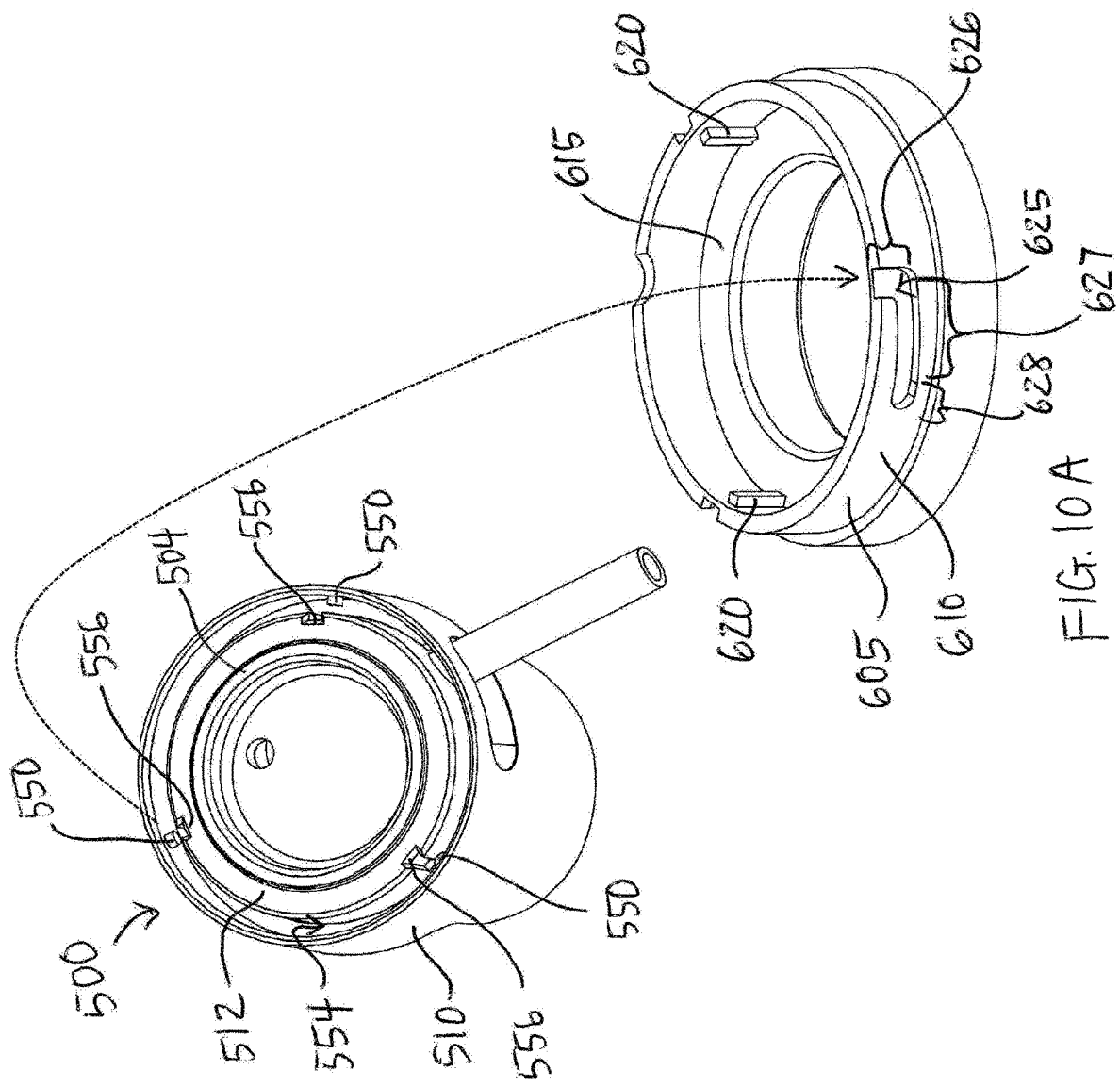

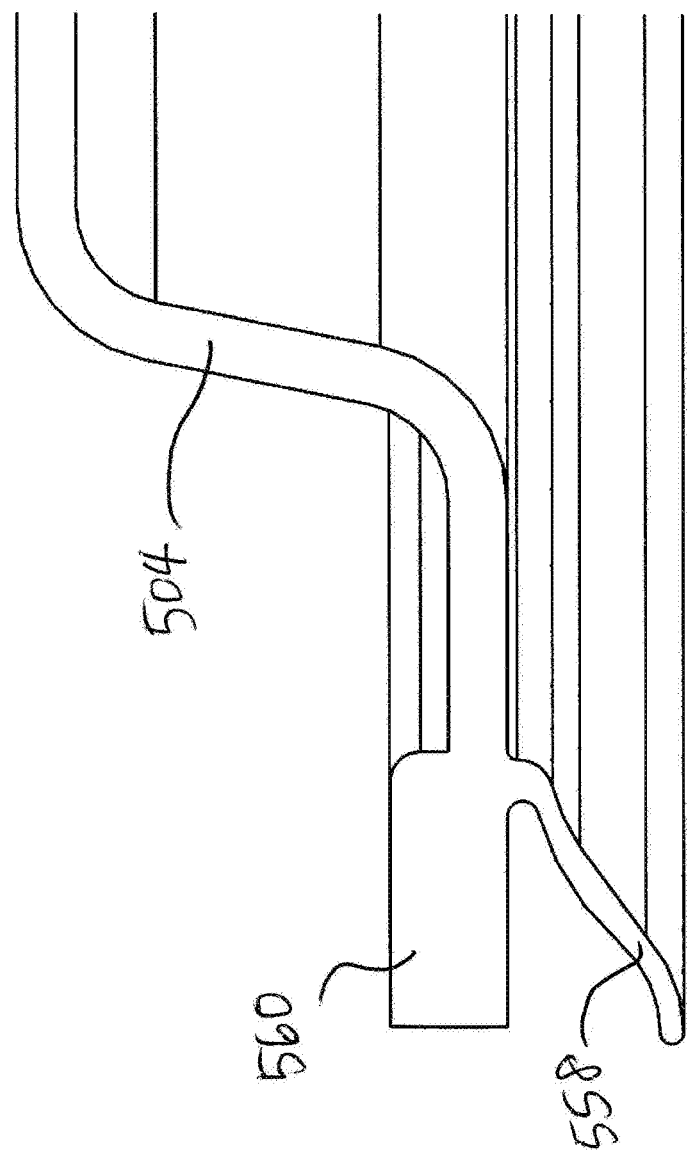

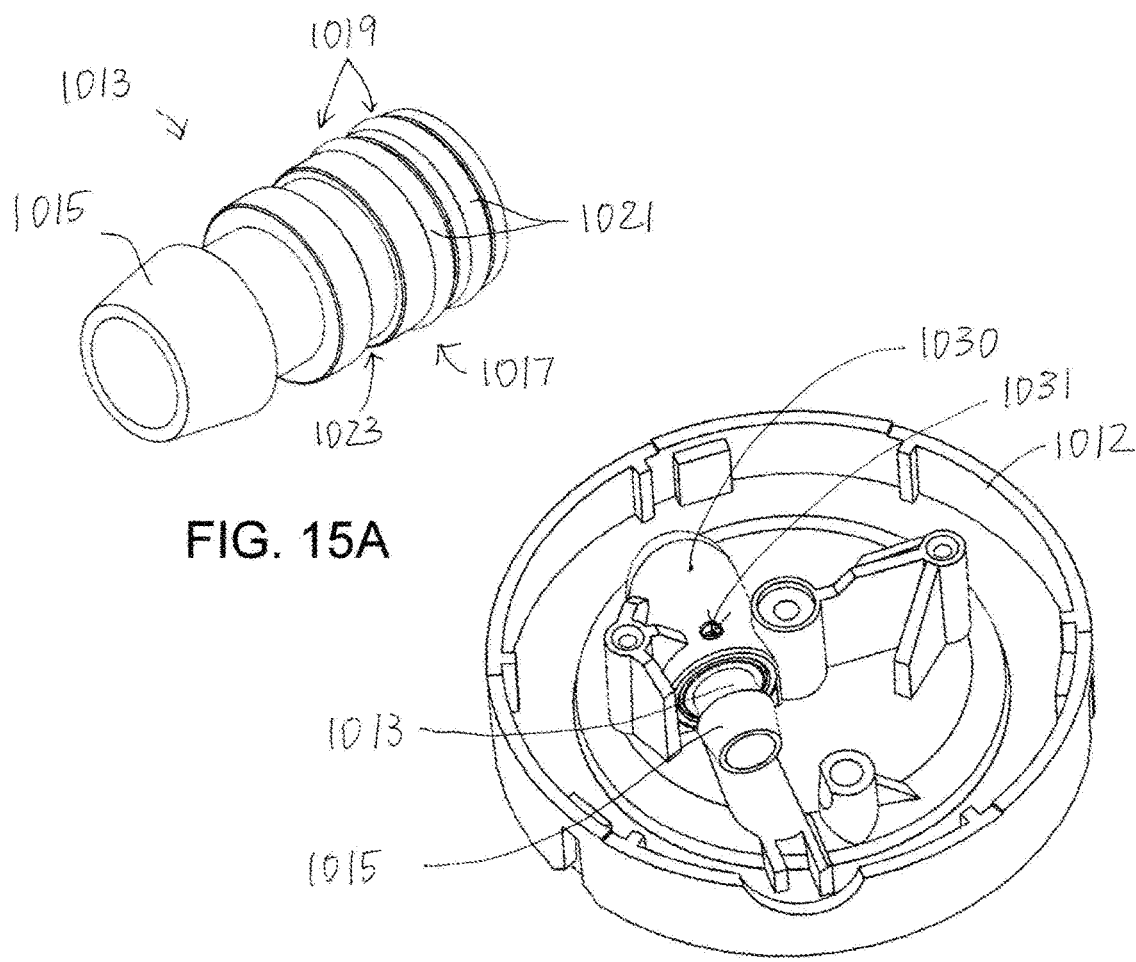
FIG. 15A
FIG. 15B
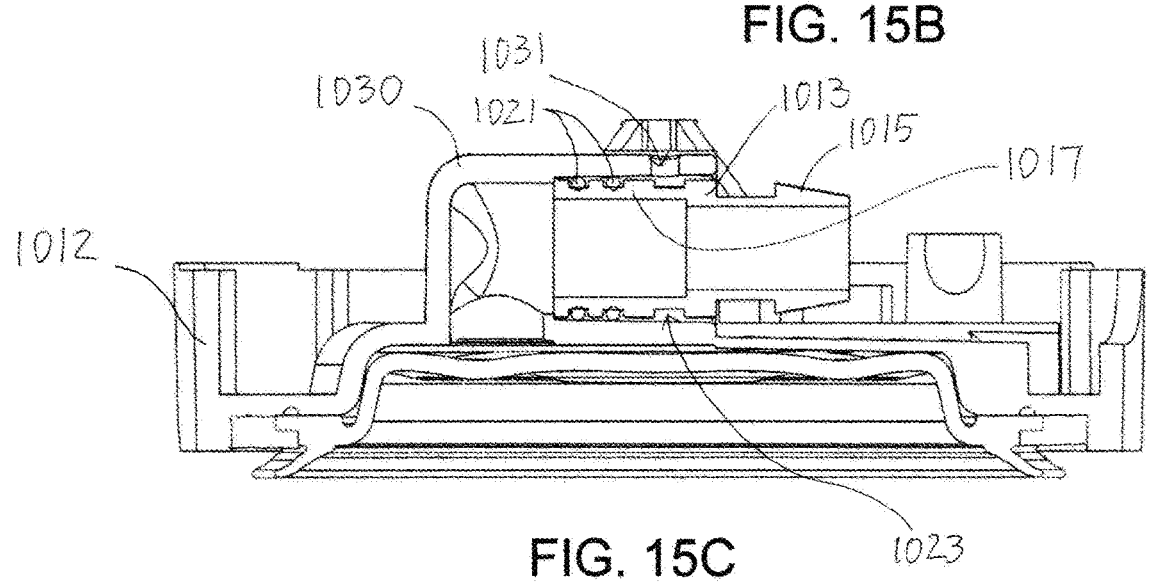
FIG. 15C

HYDRAULIC PUMPING SYSTEM FOR EXPRESSION OF BREAST MILK

CROSS-REFERENCE

The present application is a non-provisional of, and claims the benefit of, U.S. Provisional Patent Application 62/329,917, filed on Apr. 29, 2016, the entire contents of which are incorporated herein by reference.

This application is related to the following co-pending provisional and non-provisional patent applications: U.S. patent application Ser. No. 14/221,113, filed on Mar. 20, 2014, now U.S. Pat. No. 9,616,156, U.S. patent application Ser. No. 14/616,557, filed on Feb. 6, 2015, U.S. patent application Ser. No. 14/793,606, filed on Jul. 7, 2015, U.S. patent application Ser. No. 14/793,613, filed on Jul. 7, 2015, U.S. patent application Ser. No. 14/793,617, filed on Jul. 7, 2015, U.S. patent application Ser. No. 14/858,924, filed on Sep. 18, 2015, now U.S. Pat. No. 9,623,160, U.S. patent application Ser. No. 15/094,690, filed on Apr. 8, 2016, U.S. patent application Ser. No. 15/094,704, filed on Apr. 8, 2016, and U.S. patent application Ser. No. 15/349,917, filed on Nov. 11, 2016, the entire contents of which are incorporated herein by reference.

BACKGROUND OF THE INVENTION

1. Field of the Invention

The present invention generally relates to medical and pediatric nutrition devices and methods, and more particularly relates to devices and methods for expression and collection of human breast milk.

Breast pumps are commonly used to collect breast milk in order to allow mothers to continue breastfeeding while apart from their children. Many existing breast pumps are pneumatic systems, wherein a tube is attached to a drive system to transmit vacuum from the drive system to a breast fluidly sealed against a breast interface. In hospital-grade pumping systems, a barrier is often placed between the breast interface and the drive system to prevent cross-contamination between the drive system and the breast interface. For example, the barrier can be a flexible membrane or a filter that can provide a barrier while facilitating pressure transmission.

Hydraulic pumping systems for breast milk expression are described in co-pending U.S. patent application Ser. Nos. 14/221,113 and 14/793,613, the entire disclosures of which are incorporated herein by reference. In the described systems, the breast interface can comprise an expandable membrane coupled to a rigid housing to form a fluid reservoir therebetween, wherein movement of a driving fluid into or out of the reservoir via actuation of the actuatable assembly can cause corresponding contraction or expansion of the membrane. The expandable membrane, when fluidly sealed against the breast, can transfer pressure to the breast, thereby causing the expression of milk from the breast. Hydraulic systems can reduce pumping force requirements, and therefore also reduce the size of the pumping device, while maintaining high pumping efficiency.

As described in U.S. application Ser. No. 14/793,613, the breast interface can be configured to removably couple to the actuatable assembly via an actuatable assembly interface, in order to prevent cross-contamination between the breast interface and the actuatable assembly and facilitate the storage and maintenance of the device. The actuatable assembly interface may comprise a flexible membrane configured to operably couple to the actuatable assembly, wherein the flexible membrane functions to both 1) transmit pressure between the actuatable assembly and the breast interface, and 2) provide a fluid barrier to prevent cross-contamination between the actuatable assembly and the breast interface. In contrast to air used to transfer pressure in pneumatic pumping systems, the driving fluid used in hydraulic systems has a higher density than the atmosphere surrounding the driving fluid. As a result, when either the breast interface or the actuatable assembly interface is positioned above the other, head pressure is applied to the membrane of the component positioned below the other, causing the membrane to "bulge" outwards. In some cases, such bulging of either membrane can present challenges to the operation of the pumping system. For example, the bulging of the membrane of the actuatable assembly interface can make it difficult for a user to couple the interface to the actuatable assembly, or the bulging of the membrane of the breast interface can make it difficult for a user to fluidly seal the breast interface against the breast.

Therefore, it would be desirable to provide hydraulic pumping systems for the expression of breast milk having improved means for removably coupling the breast interface to the actuatable assembly. In particular, it would be desirable to provide means to fluidly decouple the breast interface and the actuatable assembly interface when the actuatable assembly interface is disconnected from the actuatable assembly.

At least some of these objectives will be satisfied by the devices and methods disclosed herein.

SUMMARY OF THE INVENTION

Hydraulic pumping systems for the expression of breast milk and methods of use thereof are disclosed herein. A pumping system in accordance with embodiments comprises a breast interface operably coupled to an actuatable assembly by means of an actuatable assembly interface. The breast interface comprises an expandable membrane coupled to a housing to form a first fluid reservoir therebetween, wherein the first fluid reservoir is coupled to a distal end of a tube carrying a driving fluid. The proximal end of the tube is coupled to the housing of the actuatable assembly interface, wherein the housing is coupled to a proximal membrane to form a second fluid reservoir therebetween. The first and second fluid reservoirs are in fluid communication via the tube, such that the driving fluid fills the space between the expandable membrane of the breast interface and the proximal membrane of the actuatable assembly interface. The actuatable assembly interface is configured to removably couple to the actuatable assembly, in order to operably couple the actuatable assembly to the proximal membrane. When the actuatable assembly interface is coupled to the actuatable assembly, actuation of the actuatable assembly causes movement of the proximal membrane moves towards and away from the breast interface, and thereby corresponding movement of the driving fluid and hence the expandable membrane towards and away from the breast, which applies negative pressure at the breast fluidly sealed against the breast interface to cause expression of milk from the breast.

The hydraulic pumping system may be configured to fluidly decouple the breast interface and the actuatable assembly interface when the actuatable assembly interface is disconnected from the actuatable assembly. For example, the actuatable assembly interface may comprise a mechanism to shut off fluid communication with the breast interface when the actuatable assembly interface is disconnected from the actuatable assembly, and re-open the fluid communication when the actuatable assembly interface is connected to the actuatable assembly. Such a mechanism may be particularly advantageous for pumping systems utilizing a driving fluid that is substantially incompressible, such as water or oil, which has a higher density than the atmosphere surrounding the driving fluid during typical use of the pumping system.

In one aspect, an apparatus for expression of breast milk from a breast comprises a breast interface configured to receive and fluidly seal against the breast, the breast interface comprising a first fluid reservoir. The apparatus further comprises an actuatable assembly interface configured to removably couple to an actuatable assembly, the actuatable assembly interface comprising a second fluid reservoir. The apparatus further comprises a tube having a first end coupled to the breast interface and a second end coupled to the actuatable assembly interface, such that the first fluid reservoir and the second fluid reservoir are in fluid communication. The first fluid reservoir, the second fluid reservoir, and the tube are filled with a driving fluid, wherein the actuatable assembly interface comprises a fluid shutoff mechanism to reversibly shut off fluid communication between the first fluid reservoir and the second fluid reservoir.

The driving fluid may have a density that is higher than the density of air, or may substantially incompressible.

The breast interface may comprise a first housing and a distal membrane coupled thereto to form the first fluid reservoir therebetween. The actuatable assembly interface may comprise a second housing and a proximal membrane coupled thereto to form the second fluid reservoir therebetween. The distal and proximal membranes may be flexible to allow movement of the driving fluid into or out of the first and second fluid reservoirs.

The proximal membrane may be configured to seal against an actuatable assembly membrane when the actuatable assembly interface is coupled to the actuatable assembly. The actuatable assembly membrane may be coupled with a driver mechanism of the actuatable assembly, such that movement of the actuatable assembly membrane in response to actuation of the driver mechanism causes corresponding movement of the proximal membrane. The proximal membrane may comprise a sealing flap configured to allow air trapped between the proximal membrane and the actuatable assembly membrane to exit.

The second housing of the actuatable assembly interface may comprise a tube receiving member configured to couple to the second end of the tube, the tube receiving member defining a bore that is in fluid communication with the second fluid reservoir through an opening in the second housing. The tube receiving member may comprise a barbed region configured to receive the tube thereover and form a fluid seal thereagainst. The actuatable assembly interface may further comprise a barbed adaptor configured to fit within and fluidly seal against the bore of the tube receiving member, the barbed adaptor comprising a barbed region configured to receive the tube thereover and form a fluid seal thereagainst.

The fluid shutoff mechanism may be configured to shut off fluid communication between the first and second fluid reservoirs in response to detachment of the actuatable assembly interface from the actuatable assembly, and re-open the fluid communication in response to attachment of the actuatable assembly interface to the actuatable assembly. The fluid shutoff mechanism may be configured to simultaneously secure coupling of the actuatable assembly interface to the actuatable assembly and release pinching of the tube to open the tube, and to simultaneously release coupling of the actuatable assembly interface to the actuatable assembly and pinch the tube closed.

The fluid shutoff mechanism may be configured to secure or release the coupling of the actuatable assembly interface to the actuatable assembly and simultaneously release or pinch the tube via rotational movement of the actuatable assembly interface with respect to the actuatable assembly.

The fluid shutoff mechanism may comprise one or more springs and one or more engaging members configured to engage the one or more springs in a first configuration when the actuatable assembly interface is detached from the actuatable assembly, or in a second configuration different from the first configuration when the actuatable assembly interface is attached to the actuatable assembly. The one or more springs may comprise one or more material springs each having a detent geometry, the detent geometry defining a first detent and a second detent configured to engage the one or more engaging members in the first configuration or in the second configuration, respectively. The one or more springs may be configured such that a greater force is required to disengage the one or more engaging members from the one or more springs in the first configuration than in the second configuration. The fluid shutoff mechanism may be configured to secure or release the coupling of the actuatable assembly interface to the actuatable assembly and simultaneously release or pinch the tube via rotational movement of the actuatable assembly interface with respect to the actuatable assembly, and the one or more springs and one or more engaging members may comprise a plurality of springs and a plurality of engaging members distributed rotationally about the actuatable assembly interface. The plurality of springs and the plurality of engaging members may be distributed in a rotationally symmetric manner about the actuatable assembly interface.

The actuatable assembly interface may comprise a keyed locking mechanism configured to allow attachment and removal of the actuatable assembly interface to and from the actuatable assembly only when the fluid communication between the first and second fluid reservoirs is shut off.

In another aspect, an apparatus for removably coupling a breast interface with an actuatable assembly comprises a housing coupled to a proximal end of a tube, wherein a distal end of the tube is fluidly coupled to a first fluid reservoir of the breast interface. The apparatus further comprises a flexible membrane coupled to the housing to form a second fluid reservoir therebetween, the second fluid reservoir in fluid communication with the first fluid reservoir via the tube. The housing comprises a fluid shutoff mechanism to reversibly shut off fluid communication between the first and second fluid reservoirs.

In another aspect, a system for expression of breast milk from a breast comprises an actuatable assembly comprising a driver mechanism coupled to an actuatable assemble membrane, and an actuatable assembly interface configured to removably couple to the actuatable assembly. The actuatable assembly interface comprises a housing and a flexible membrane coupled together to form a second fluid reservoir therebetween. The second fluid reservoir of the actuatable assembly interface is in fluid communication with a first fluid reservoir of a breast interface via a tube. The housing comprises a fluid shutoff mechanism to reversibly shut off fluid communication between the first and second fluid reservoirs.

The flexible membrane may be configured to seal against the actuatable assembly membrane when the actuatable assembly interface is coupled to the actuatable assembly, such that movement of the actuatable assembly membrane in response to actuation of the driver mechanism causes corresponding movement of the flexible membrane. The flexible membrane may comprise a sealing flap configured to expel air trapped between the flexible membrane and the actuatable assembly membrane when the driver mechanism moves the actuatable assembly membrane towards the flexible membrane. The actuatable assembly may comprise a receiving surface configured to receive the actuatable assembly interface, the receiving surface defining an sealing surface configured to seal against the sealing flap and an annular rib disposed about the outer periphery of the sealing surface. The annular rib may be vertically offset from the sealing surface by a height predetermined to allow sufficient movement of the sealing flap to expel the air trapped between the flexible membrane and the actuatable assembly membrane.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4A illustrates an exemplary embodiment of a hydraulic pumping system, wherein the breast interface and the actuatable assembly interface are positioned at an equal height.

FIG. 4B illustrates the exemplary embodiment of the hydraulic pumping system of FIG. 4A, wherein the breast interface is positioned above the actuatable assembly interface.

FIG. 4C illustrates the exemplary embodiment of the hydraulic pumping system of FIG. 4A, wherein the breast interface is positioned above the actuatable assembly interface, while fluid communication between the breast interface and the actuatable assembly interface is shut off.

FIG. 6A is an isometric view of the locking ring assembly of the actuatable assembly interface of FIG. 5.

FIG. 6B is a top view of the locking ring assembly of the actuatable assembly interface of FIG. 5.

FIGS. 10A-10B illustrate the locking of the actuatable assembly interface of FIG. 5 onto a locking portion of an actuatable assembly.

FIG. 11 is a cross-sectional view of a flexible actuatable assembly interface membrane suitable for incorporation with a hydraulic pumping system as disclosed herein.

FIG. 15A shows a barbed adaptor suitable for incorporation with an actuatable assembly interface as described herein.

FIG. 15B shows the barbed adaptor of FIG. 15A coupled to an actuatable assembly interface in accordance with embodiments.

FIG. 15C is a side cross-sectional view of the actuatable assembly interface of FIG. 15B.

DETAILED DESCRIPTION OF THE INVENTION

Specific embodiments of the disclosed devices and methods will now be described with reference to the drawings. Nothing in this detailed description is intended to imply that any particular component, feature, or step is essential to the invention.

The exemplary embodiments disclosed herein are preferably directed at expression of breast milk, but one of skill in the art will appreciate that this is not intended to be limiting and that the devices, systems and methods disclosed herein may be used for other treatments requiring application of a differential pressure.

Figure 1:
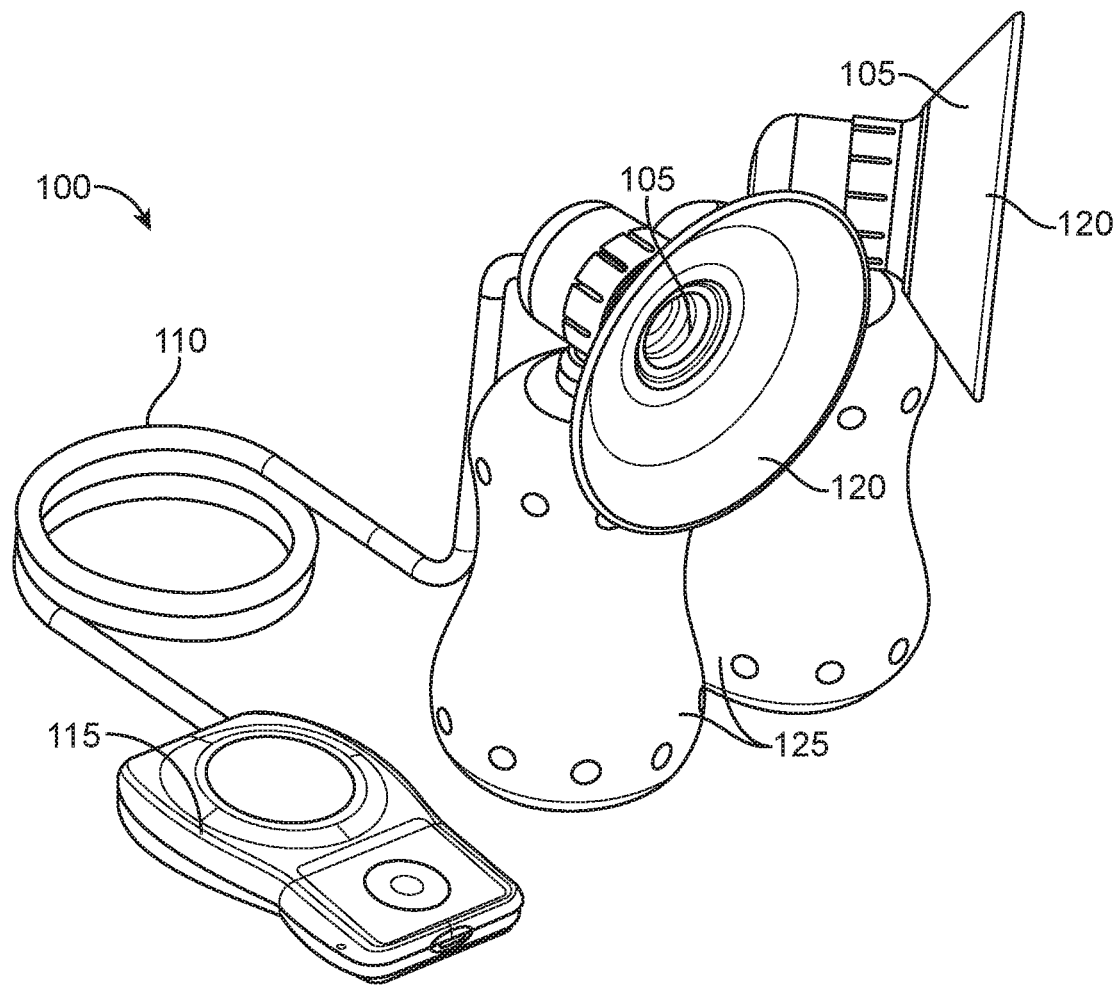
FIG. 1 illustrates an exemplary embodiment of a breast milk expression apparatus or pumping device in accordance with embodiments.

FIG. 1 illustrates an exemplary embodiment of a breast milk expression apparatus or pumping device in accordance with embodiments. Pumping device 100 (also known as an "expression apparatus") includes breast interfaces 105, a tube 110, and a controller 115 operatively coupled to breast interfaces 105 through tube 110. Breast interfaces 105 include resilient and conformable flanges 120, for engaging and creating a fluid seal against the breasts. Each breast interface 105 is fluidly coupled to a collection vessel 125 configured to receive the expressed breast milk. Each breast interface 105 is additionally coupled to one or more controllers 115 that house the power source and drive mechanism for the pumping device 100. For example, the controller 115 may comprise an actuatable assembly for generating negative and/or positive pressure at the breast interface to cause expression of milk from a breast fluidly sealed against the breast interface. Tube 110 may transmit suitable energy inputs, such as mechanical energy generated by an actuatable assembly housed within the controller, from controller 115 to breast interfaces 105. Breast interfaces 105 can then convert the energy inputs into pressure applied against the breasts in a highly efficient manner, resulting in the expression of milk into collection vessels 125. For example, as described in further detail herein, the breast interface may comprise an expandable membrane coupled to a rigid housing, wherein the expandable member expands and contracts in response to actuation of the actuatable assembly apply pressure at the breast and thereby cause expression of milk from the breast.

The controller 115 may further comprise hardware for various functions, such as controlling the pumping device 100, quantifying milk expression, measuring or analyzing data related to characteristics of the expressed milk, and/or communicating with other devices. For example, the controller may be configured to communicate with one or more personal computing devices such as smartphones, tablets, or personal computers, wherein the personal computing device may be configured to provide a user interface for a user to interact with the pumping device.

The device 100 may further comprise one or more sensors configured to track various characteristics of the collected fluid, such as the quantity of the fluid or a composition of the fluid. The one or more sensors may be coupled to one or more portions of the breast interfaces or the collection vessels, or they may be coupled to controller. Power may be provided to the one or more sensors via a connection to the controller 115, or to another source of power. In embodiments in which the one or more sensors are coupled to one or more portions of the breast interfaces 105 or collection vessels 125, the sensors may be further coupled to the controller 115 via one or more communication lines configured to transmit signals between the sensors and the controller.

One of skill in the art will appreciate that components and features of this exemplary embodiment can be combined or substituted with components and features of any of the embodiments of the present invention as described below. Similarly, components and features of other embodiments disclosed herein may be substituted or combined with one another.

Figure 2:
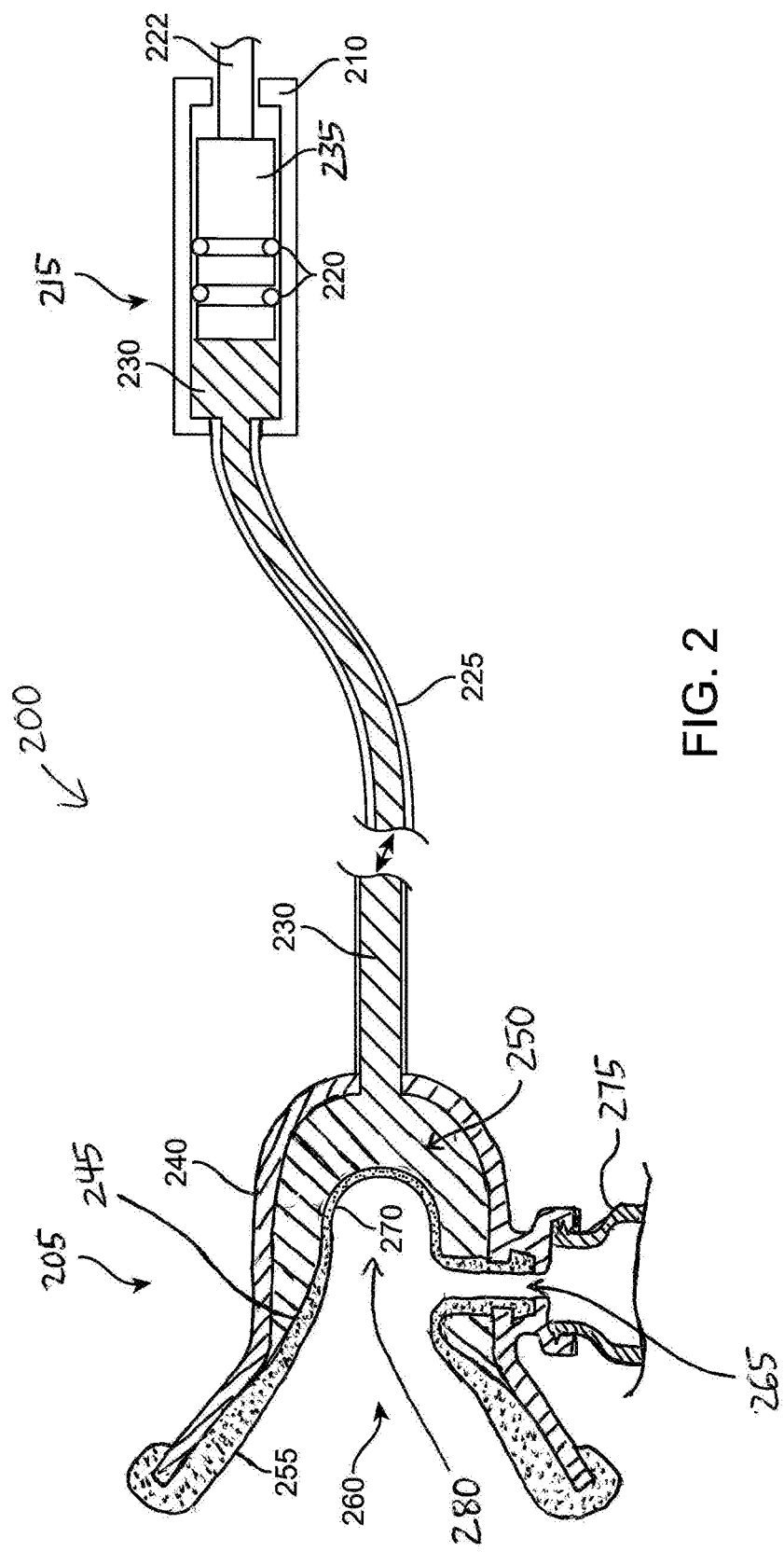
FIG. 2 illustrates an exemplary embodiment of a hydraulic pumping system.

FIG. 2 illustrates an exemplary embodiment of a hydraulic pumping system 200. The hydraulic pumping system comprises a breast interface 205 and an actuatable assembly 215, operably coupled together by a tube 225 carrying a driving fluid 230.

The breast interface 205 comprises an interface housing 240 and an expandable membrane 245 coupled together to form a reservoir 250 therebetween. The housing 240 can be coupled to a distal end of the tube 225, such that the reservoir 250 is in fluid communication with the tube and can be filled with the driving fluid 230. The expandable membrane 245 comprises a flange or sealing portion 255 configured to fluidly seal against a breast received within the breast interface, and an expandable or deformable portion 270 configured to expand and contract in response to the removal and addition of driving fluid 230 from/to the reservoir 250. The sealing portion 255 may comprise a thickness greater than the thickness of the deformable portion 270, as shown. The expandable membrane may have a distal opening 260 through which the nipple and/or surrounding breast tissue is received, and proximal opening or drain port 265 through which expressed breast milk may exit the breast interface and enter a collection vessel 275 coupled to the breast interface. An expression area 280 may be defined between the distal opening and the proximal opening, wherein the milk is expressed from the breast into the expression area, then subsequently collected into the collection vessel through the drain port. Optionally, a one-way valve such as a flap, duckbill, or ball valve may be disposed over the drain port 265 to provide passage of milk into the collection vessel 275 while maintaining vacuum pressure in expression area 280.

The actuatable assembly 215 may comprise an assembly housing 210, a driving element 235, radial seals 220, and a shaft 222. Driving element 225 may be operatively coupled to a controller, such as controller 115 of FIG. 1, through shaft 222.

In operation, actuation of the actuatable assembly 215 displaces the driving fluid 230 contained within tube 225, which can be a flexible line. Fluid 230 occupies reservoir 250 within breast interface 205 and is coupled with expandable membrane 245. The deformable portion 270 of the expandable membrane 245 can be configured to expand or move towards the housing 240 in response to the displacement of the driving fluid out of the reservoir, and contract or move away from the housing in response to displacement of the driving fluid into the reservoir. When the expandable membrane expands, the membrane moves away from the breast received within the breast interface, thereby creating negative pressure at the breast. When the expandable membrane contracts, the membrane moves towards the breast, thereby increasing the pressure at the breast to return the pressure to a baseline level prior to the expansion of the expandable membrane. Thus, when a breast is engaged into and fluidly sealed against the sealing element 255 of the expandable membrane, displacement of the driving element 235 in the proximal direction away from the breast can produce substantial vacuum pressure against the breast through the deformable portion of the expandable membrane, resulting in the expression of breast milk into the expression area 280. The expressed milk drains through drain port 265 into collection vessel 275.

The reservoir 250 can therefore provide a sole source of negative pressure for the breast interface, wherein movement of the fluid 230 in or out of the reservoir and corresponding movement of the membrane 245 towards or away from the breast can generate sufficient negative pressure against the breast to cause the expression of milk, without the aid of additional pressure sources such as air suction applied directly to the nipple. The driving fluid may comprise any suitable fluid for transferring sufficient pressure from the actuatable assembly to the expandable membrane to cause expression of milk from the breast. In many embodiments, the driving fluid may be as a substantially incompressible fluid, such as water or oil. Suitable incompressible fluids for hydraulic systems are known to those of skill in the art.

The expandable membrane 245 may comprise a flexible or elastic material allowing the membrane to elastically deform in response to the actuation of the pumping mechanism. For example, the expandable membrane may comprise one or more of silicone, polyether block amides such as PEBAX, or polychloroprenes such as neoprene, and can have a specified thickness and durometer. Alternatively or additionally, the expandable membrane 245 may comprise a membrane having one or more corrugated features (such as pleats) that allow expansion and contraction of the membrane. The expandable membrane having the one or more corrugated features may comprise an elastically deformable material or a substantially rigid material, such as stainless steel, nitinol, high durometer polymer, or high durometer elastomer. The one or more corrugated features can provide stress and/or strain distribution to enable the substantial deformation of the expandable membrane without surpassing the yield point of the material. The amount of deformation of the expandable membrane can be controlled by many factors, (e.g., wall thickness, durometer, surface area) and can be optimized based on the pumping device (e.g., pump power, vacuum requirements).

One of skill in the art will appreciate that components and features of any of the exemplary embodiments of the hydraulic pumping system can be combined or substituted with components and features of any of the embodiments of the present invention as described herein.

An actuatable assembly for a breast milk expression device as described herein can be configured to removably couple to the breast interface assembly, so as to keep the driving fluid carried in the transmission lines (such as the tube described herein) and in the breast interface physically separate from the actuatable assembly. Such a physical separation between the actuatable assembly and the fluid in the breast interface can help prevent cross-contamination between the breast interface and the actuatable assembly. Further, the easy separation of various components of the expression device can facilitate the storage and maintenance of the device.

Figure 3A:
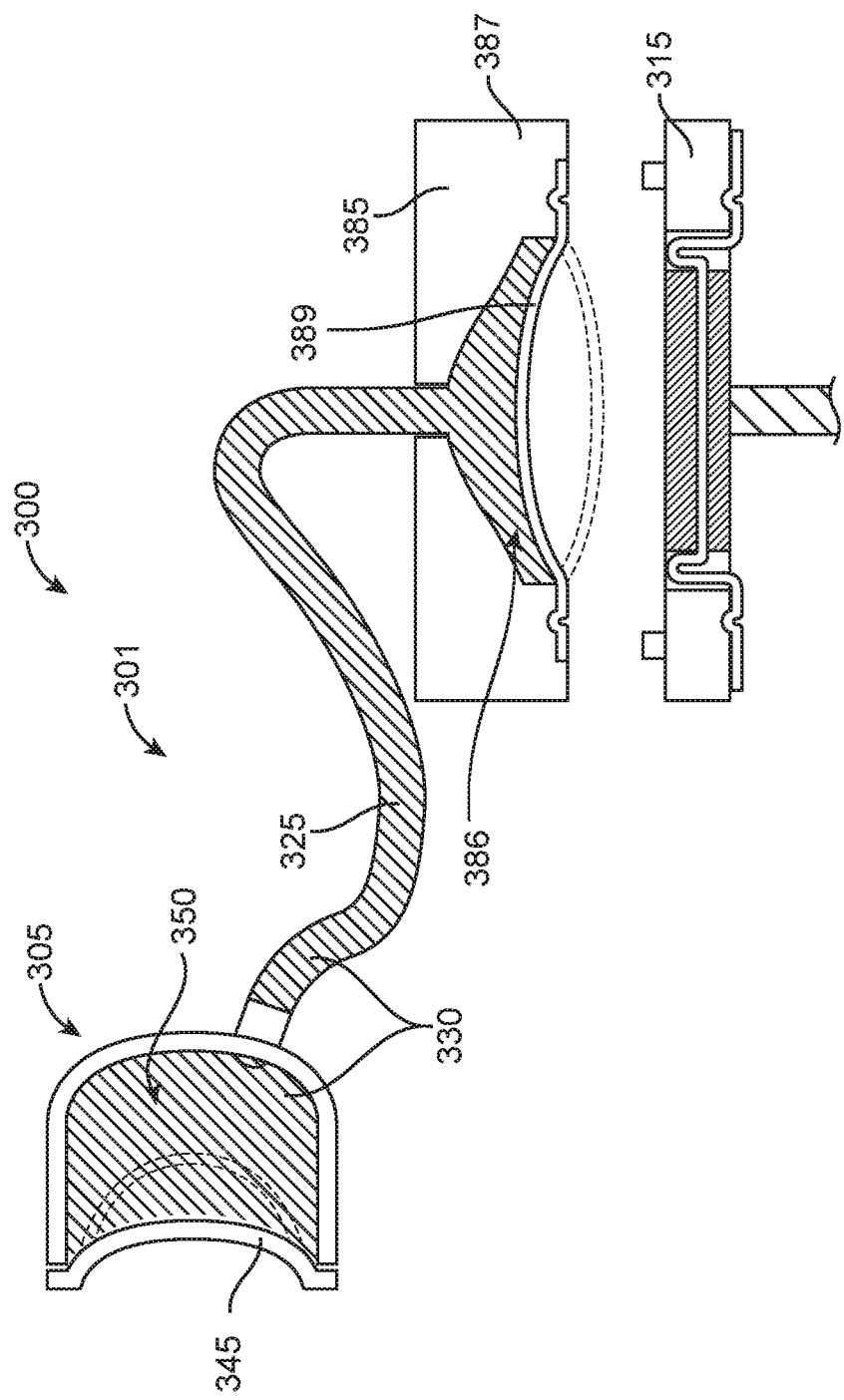
FIG. 3A is a cross-section of an exemplary embodiment of a hydraulic pumping system comprising an actuatable assembly interface.

FIG. 3A is a cross-section of an exemplary embodiment of a hydraulic pumping system 300 comprising an actuatable assembly interface 385. The actuatable assembly interface (AAI) 385 can removably couple to the actuatable assembly 315, so as to operatively couple the actuatable assembly to the breast interface 305, while keeping the mechanisms of the actuatable assembly separate from the fluid 330 in the tubing 325 and in the fluid reservoir 350 of the breast interface 305. The AAI 385 may comprise a flexible membrane 389 coupled to a housing 387 to form a fluid reservoir 386 therebetween. The AAI fluid reservoir 386 may be in fluid communication with the breast interface fluid reservoir 350 via the tube 325, such that the fluid 330 can move into and out of the reservoir 386. When the AAI 385 is coupled to the actuatable assembly 315, the actuation of the actuatable assembly can cause movement of the AAI membrane 389, in turn causing the fluid 330 to be pulled into or pushed out of the AAI fluid reservoir 386. This, in turn, causes the fluid 330 to be pulled out of or pushed into the fluid reservoir 350 of the breast interface, thereby causing an expandable membrane 345 of the breast interface to apply pressure to the breast engaged into the breast interface. Thus, the flexible AAI membrane 389 can function to both transmit pressure between the actuatable assembly and the breast interface, and provide a fluid barrier to prevent cross-contamination between the actuatable assembly and the breast interface. The breast interface 305, AAI 385, and tubing 325 can collectively form the breast shield assembly 301, an enclosed, fluidly sealed assembly that can easily attach to and detach from an actuatable assembly to transfer pressure from the actuatable assembly to a breast.

Figure 3B:
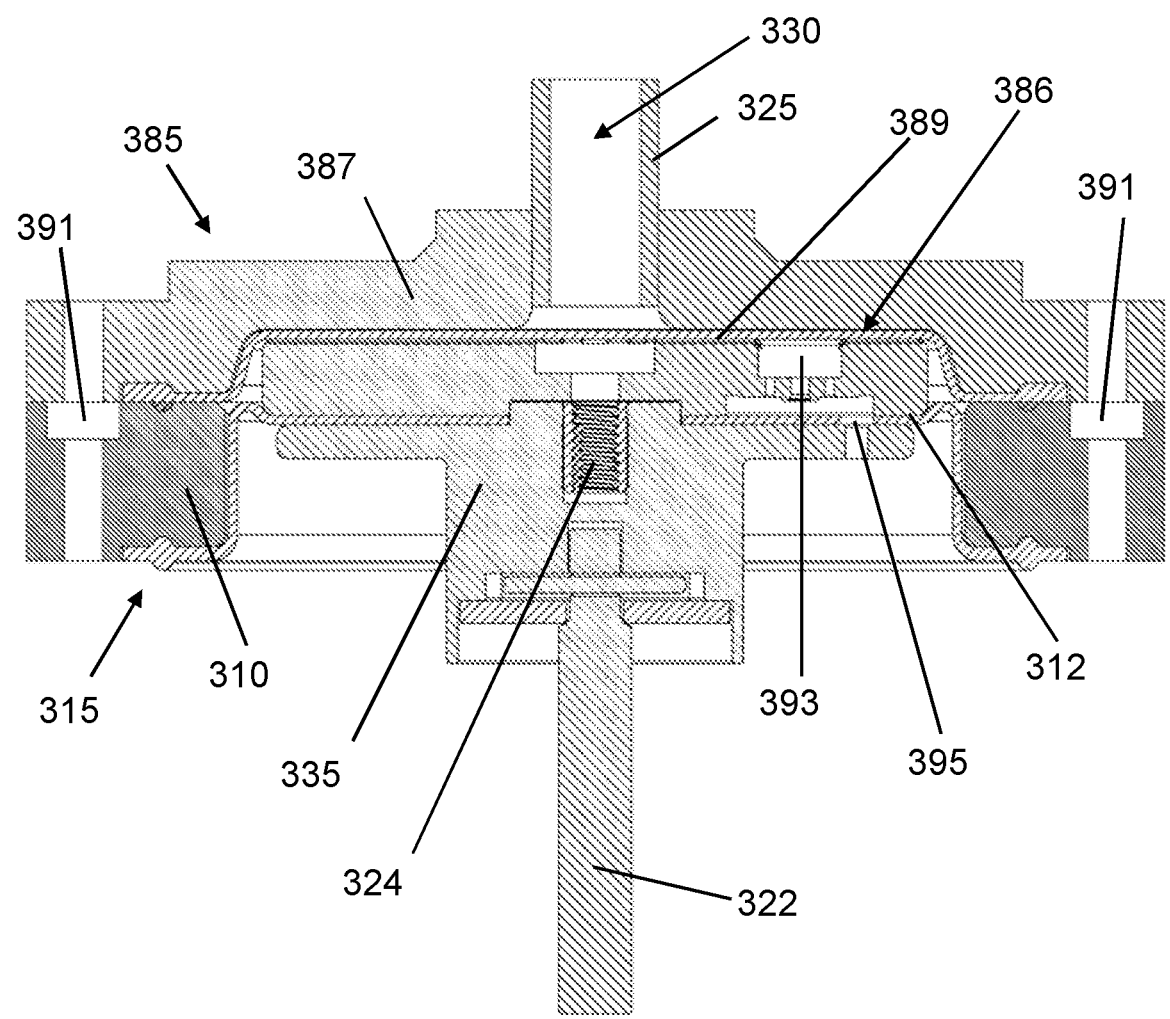
FIG. 3B is a cross-section of an actuatable assembly coupled to the actuatable assembly interface of FIG. 3A.

FIG. 3B is a cross-section of an actuatable assembly 315 coupled to an actuatable assembly interface 385, as illustrated in FIG. 3A. The actuatable assembly interface (AAI) 385 comprises an actuatable assembly interface house (AAI housing) 387 and a flexible actuatable assembly interface membrane (AAI membrane) 389 coupled thereto to form a fluid reservoir 386 therebetween. The AAI housing is configured to couple to tubing 325, which is fluidly coupled to the fluid reservoir of the breast interface. The tubing 325 is operatively coupled to the AAI membrane 389, such that movement of the AAI membrane causes movement of the driving fluid 330 carried by the tubing. The actuatable assembly 315 comprises an actuatable assembly housing (AA housing) 310 and an actuatable assembly membrane (AA membrane) 312 coupled thereto. The AA membrane is operatively coupled to the driver mechanism 335 of the actuatable assembly, such that actuation of the driver mechanism causes movement of the membrane 312. The driver mechanism may comprise any pump mechanism as described herein or as known in the art. For example, the driver mechanism may comprise a piston assembly shown in FIG. 3B, the piston configured to move in response to movement of the lead screw 322 driven by a motor.

The AA housing 310 may be configured to removably couple to the AAI housing 385, for example via one or more magnets 391 as shown. The magnets may be embedded in the AAI housing, the AA housing, or both; accordingly, one or more of the AAI housing and the AA housing may comprise a metal material configured to be attracted to the magnets. The actuatable assembly may further comprise an alignment mechanism 324, such as pins or screws configured to engage a portion of the AAI, in order to ensure correct alignment of the actuatable assembly with the AAI.

When the actuatable assembly and the AAI are coupled together, the AA membrane 312 and the AAI membrane 389 are brought into communication with one another. As the motor of the actuatable assembly is actuated, the driver mechanism 335 pushes the membrane 312 upward toward the AAI membrane 389, causing at least a portion of the air trapped between the two membranes to be pushed out via a one-way valve 393 coupled to either the actuatable assembly or the AAI. In order to ensure that the AAI does not separate from the actuatable assembly during coupling of the two members, the magnets 391 may be configured to have a magnetic force that is greater than the exit force of air from the one-way valve. Once the trapped air is pushed out through the valve outlet 395, the AAI membrane 389 becomes operatively coupled to the AA membrane 312, such the AAI membrane will follow the cyclical motions of the AA membrane as the actuatable assembly is actuated. Movement of the AAI membrane 389 will cause corresponding movement of the driving fluid 330 in the tubing 325, causing fluid to be removed from or added to the fluid reservoir in the breast interface.

FIG. 4A illustrates an exemplary embodiment of a hydraulic pumping system 400 comprising a breast shield assembly 401, wherein the breast interface 405 and the actuatable assembly interface (AAI) 485 are positioned at an equal height. As described herein, the breast interface comprises an expandable membrane 445, also referred to herein as the distal membrane of the pumping system, and the AAI comprises a flexible membrane 489, also referred to herein as the proximal membrane of the pumping system. The distal and proximal membranes are operably coupled together with the driving fluid 430, which is transferred between the first fluid reservoir 450 of the breast interface and the second fluid reservoir 486 of the AAI via the tubing 425. When the breast interface and the AAI are positioned at an equal height, no significant head pressure is applied to either the distal membrane or the proximal membrane, and the membranes take their default resting positions as shown in FIG. 4A. In particular, the proximal membrane 489 sits flush against the inner surface of the AAI housing 487, with minimal fluid volume present inside the fluid reservoir 486, such that the AAI can easily be placed over and coupled to the actuatable assembly.

FIG. 4B illustrates the exemplary embodiment of the hydraulic pumping system 400 of FIG. 4A, wherein the breast interface 405 is positioned above the AAI 485. In contrast to air used to transfer pressure in pneumatic pumping systems, the driving fluid 430 used in the hydraulic pumping system has a higher density than the atmosphere surrounding the driving fluid. As a result, when either the breast interface or the actuatable assembly interface is positioned above the other, head pressure is applied to the membrane of the component positioned below the other, causing the membrane to distend or "bulge" outwards. For example, as shown in FIG. 4B, when the breast interface is positioned above the AAI, head pressure 490 is applied to the proximal membrane 489, causing distension of the proximal membrane in the downward direction. Such bulging of the proximal membrane can make it difficult for a user to couple the interface to the actuatable assembly, as the driving fluid needs to be pushed out of the AAI in order to be able to align and couple the AAI with the actuatable assembly. In addition, the movement of the driving fluid from the breast interface to the AAI causes a corresponding reduction in volume of the fluid reservoir 450 of the breast interface, formed between the breast interface housing 440 and the distal membrane 445, and expansion of the distal membrane as shown. Fluidly sealing a breast against the breast interface while the distal membrane is expanded as such, and subsequently actuating the actuatable assembly to begin pumping, may result in inefficient expression of milk, since the distal membrane is already in an expanded configuration and may not be able to expand substantially further to effectively create negative pressure at the breast.

FIG. 4C illustrates the exemplary embodiment of the hydraulic pumping system 400 of FIG. 4A, wherein the breast interface 405 is positioned above the AAI 485, while fluid communication between the breast interface and the AAI is shut off. Shutting off fluid communication between the breast interface and the AAI, such as in manner 492 as shown, effectively decouples the distal membrane 445 from the proximal membrane 489. In this configuration, even when the breast interface is positioned above the AAI, the driving fluid 430 is unable to move from the fluid reservoir 450 at the breast interface into the fluid reservoir 486 at the AAI to push against the proximal membrane 489. Thus, shutting off fluid communication between the breast interface and the AAI while the pumping system is inactive can help ensure that: 1) the distal breast interface membrane is in the proper configuration for beginning pumping; and 2) the proximal AAI membrane is in the proper configuration for coupling the AAI to the actuatable assembly.

The AAI may be configured in one of many ways to shut off fluid communication between the breast interface and the AAI when the AAI is disconnected from the actuatable assembly, then re-establish the fluid communication once the AAI is connected to the actuatable assembly. Preferably, the AAI and/or the actuatable assembly comprise a mechanism to automatically shut-off or re-establish fluid communication between the breast interface and the AAI in response to the decoupling and coupling, respectively, of the AAI to the actuatable assembly, without requiring separate action from a user to toggle the fluid communication on and off.

Figure 5:
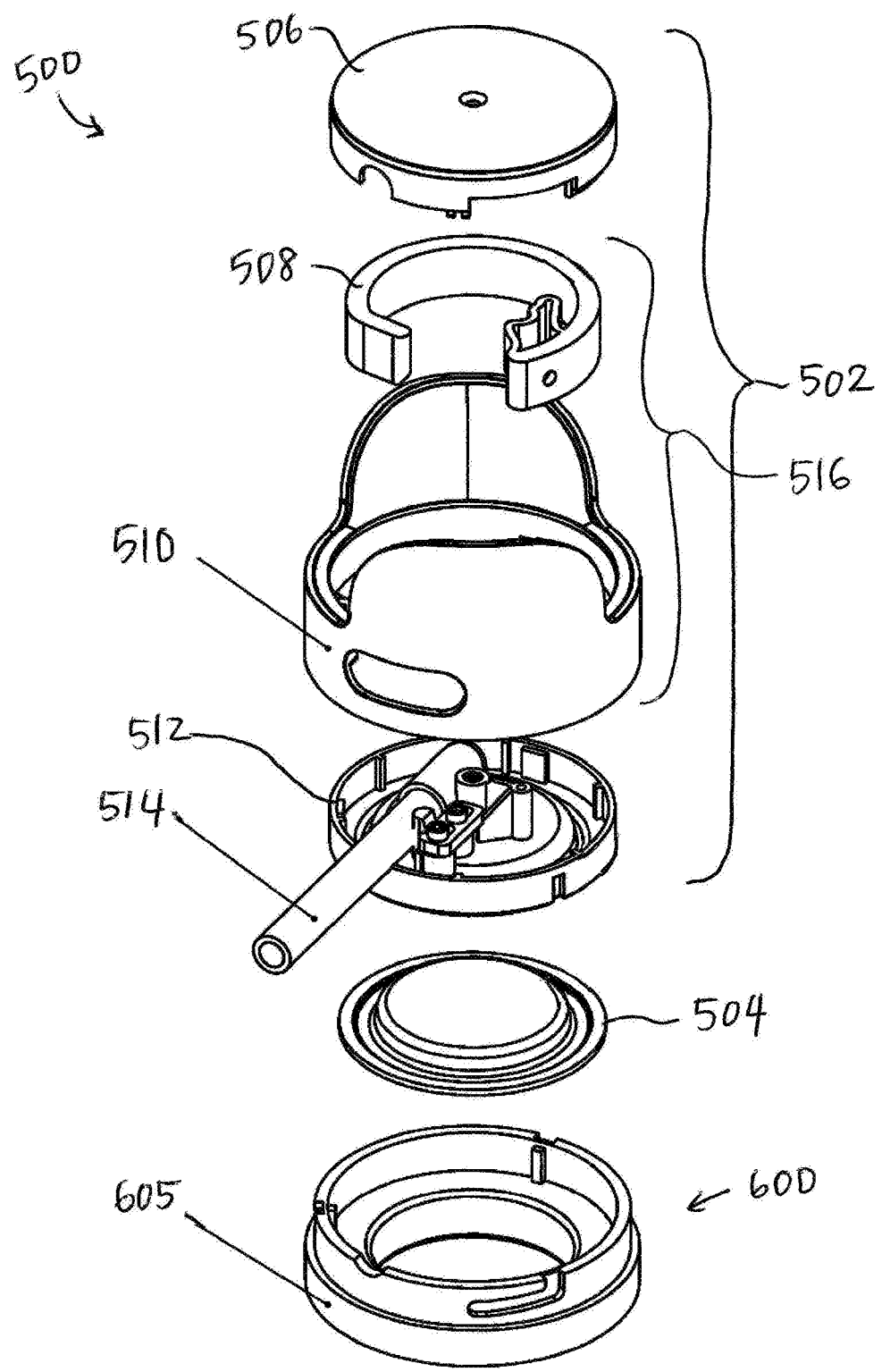
FIG. 5 is an exploded view of an exemplary embodiment of an actuatable assembly interface coupled to an actuatable assembly.

FIG. 5 is an exploded view of an exemplary embodiment of an actuatable assembly interface (AAI) 500 coupled to an actuatable assembly 600. The AAI 500 comprises a housing 502 and a flexible AAI membrane 504, also referred to herein as proximal membrane. The housing 502 comprises one or more components collectively configured to provide a locking mechanism for locking onto a corresponding locking portion 605 of the actuatable assembly 600. In the embodiment shown in FIG. 5, the housing 502 comprises a cover 506, an internal locking ring 508, an external locking ring 510, and a base 512. The AAI membrane 504 can be coupled to the bottom of the base 512. Tube 514, carrying the driving fluid for the pumping system and fluidly coupling the AAI to a breast interface, can also be coupled to the AAI via the base 512. The cover can be keyed and coupled to the base. The internal locking ring and external locking ring together form the locking ring assembly 516, which can rotate with respect to the base and the cover to provide a fluid communication shut-off mechanism, as described in further detail herein. The locking ring assembly can also rotate with respect to the locking portion 605 to lock the AAI onto the actuatable assembly. The AAI may be rotationally symmetric in shape to provide a rotational locking mechanism for coupling onto the actuatable assembly, wherein the AAI can be coupled to or decoupled from the actuatable assembly via rotational movement of the AAI with respect to the actuatable assembly. For example, as shown, components of the AAI such as the base, cover, locking ring assembly, and AAI membrane may have a generally circular footprint, and the locking portion of the actuatable assembly may have a corresponding shape to receive the AAI.

FIG. 6A is an isometric view and FIG. 6B is a top view of the locking ring assembly 516 comprising the internal locking ring 508 and external locking ring 510 of the AAI 500. The internal locking ring and external rocking ring may be coupled together so as to rotate together. For example, the external locking ring 510 may comprise one or more torque transmission members 518, such as protrusions extending radially inwards towards the internal locking ring. The torque transmission members may transmit torque to the internal locking ring by pushing onto the internal locking ring, or the internal locking ring may comprise one or more grooves, indents, holes, or other mechanisms for receiving the torque transmission members. Optionally, the internal and external locking rings may be formed as a single component, rather than as separate components that are coupled together.

The external locking ring may comprise one or more handling portions 520 to facilitate manipulation of the locking ring assembly by a user. For example, as shown, the handling portions may comprise one or more regions protruding upwards. Alternatively or additionally, the handling portions may comprise handles, knobs, radial protrusions, indented regions, textured outer surfaces, or any other suitable means of facilitating the grabbing and rotating of the locking ring assembly by a user.

The internal locking ring may comprise a partial ring having two ends, wherein a first end may comprise a fluid communication shutoff mechanism such as a material spring 522. The material spring may comprise a detent geometry, which may be built into the material spring as shown. Alternatively, the spring may comprise separate components that function as detents, such as ball plungers or leaf fingers. The detent geometry can comprise an open detent 524 and a shutoff detent 526, wherein the open detent and the shutoff detent are configured to alternatingly hold a corresponding engaging element of the base. When AAI is not locked onto the actuatable assembly, the engaging element is held in the shutoff detent, and fluid communication between the breast interface and the AAI is shut off. When the AAI is fully locked onto the actuatable assembly, the engaging element is held in the open detent, and fluid communication between the breast interface and the AAI is re-opened. The second end of the internal locking ring may comprise a tip 528 configured to push against the tube carrying the driving fluid, thereby pinching the tube shut, when an engaging element is held in the shutoff detent 526. As shown in FIGS. 6A and 6B, the open detent 524 and the shutoff detent 526 may have slightly different sizes or shapes, such that a different amount of force is required for an engaging element to move from the open detent to the shutoff detent than to move from the shutoff detent to the open detent. Preferably, the detent geometry is configured to require greater force for an engaging element to move from the shutoff detent to the open detent, than from the open detent to the shutoff detent. For example, the open detent can comprise a shallower indentation than the shutoff detent, or the two detents may comprise materials with varying stiffness or other material properties. Such a configuration can prevent accidental movement of the engaging element from the shutoff detent to the open detent, to help ensure that while the AAI is not locked onto the actuatable assembly (e.g., during storage of the pumping system), the fluid communication between the breast interface and the AAI remains securely shut off.

Figure 7A:
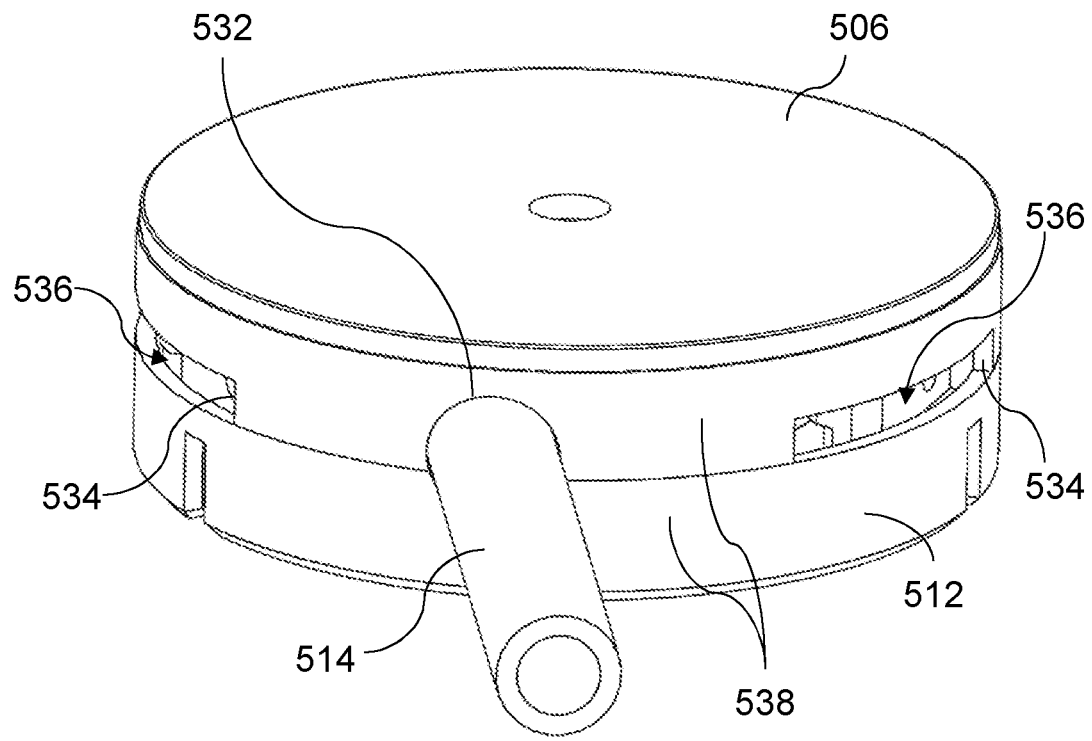
FIG. 7A shows the cover, base, and tube of the actuatable assembly interface of FIG. 5 assembled together.

FIG. 7A shows the cover 506, base 512, and tube 514 of the actuatable assembly interface (AAI) 500 assembled together. As described herein, the tube 514 carrying the driving fluid for the hydraulic pumping system is coupled to the base 512. The cover 506 may comprise a rounded notch 532 disposed along the bottom edge of the rounded side wall, configured to be positioned over the tube 514 when the cover is coupled to the base, such that the tube 514 coupled to the base is allowed to protrude from the base-cover assembly without being pinched or deformed by the cover. The cover may further comprise one or more rectangular notches 534 disposed along the bottom edge of the side wall. The one or more rectangular notches can form windows 536 when the cover is coupled to the base. In the complete AAI assembly, the internal locking ring 508 is disposed within the base-cover assembly shown in FIG. 7A, while the external locking ring 510 is disposed about the periphery of the base-cover assembly. The one or more windows 536 can function to allow the torque transmitting members 518 of the external locking ring 510, as shown in FIGS. 6A and 6B, to pass from the external locking ring to the inside of the base-cover assembly to connect with the internal rotating ring 508. The number and positions of the rectangular notches 534, and hence windows 536, may be configured to match the number and positions of torque transmitting members. To lock the AAI onto the actuatable assembly or unlock the AAI from the actuatable assembly, the external locking ring is rotated about the base-cover assembly while the base is engaged with the locking portion of the actuatable assembly. The side walls of the base and the cover provide bearing surfaces 538 for the external locking ring during the rotation of the external locking ring. The windows 536 may extend over a sufficient length to allow rotation of the torque transmitting members within the windows while the AAI is locked onto or unlocked from the actuatable assembly.

Figure 7B:
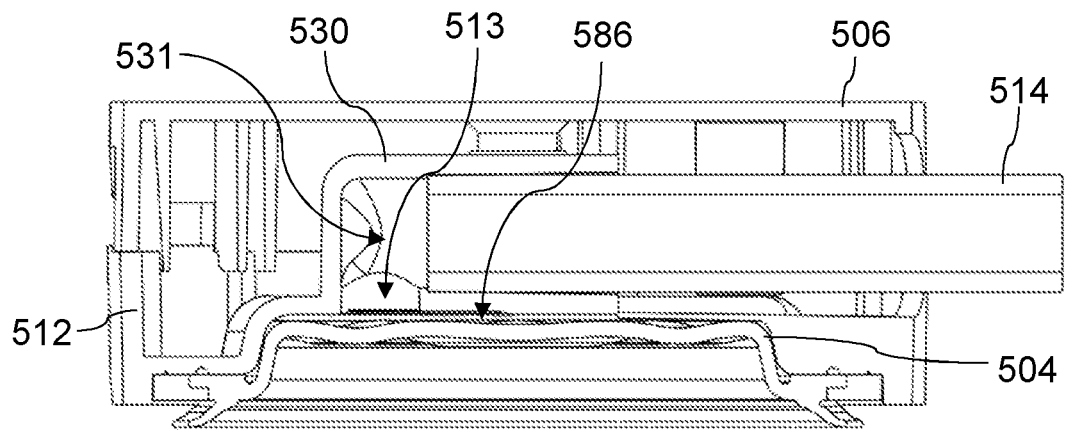
FIG. 7B is a side cross-sectional view of the partial assembly of the actuatable assembly interface shown in FIG. 7A.

FIG. 7B is a side cross-sectional view of the partial assembly of AAI 500 shown in FIG. 7A. The base 512 comprises a tube receiving member 530 configured to couple to the tube 514. The tube receiving member 530 may define a bore 531 sized and shaped to receive the tube 514 therein, wherein the bore is in fluid communication with the fluid reservoir 586 of the AAI 500, formed between the AAI membrane 504 and the base 512, through an opening 513 formed through the bottom of the base.

Figure 8A:
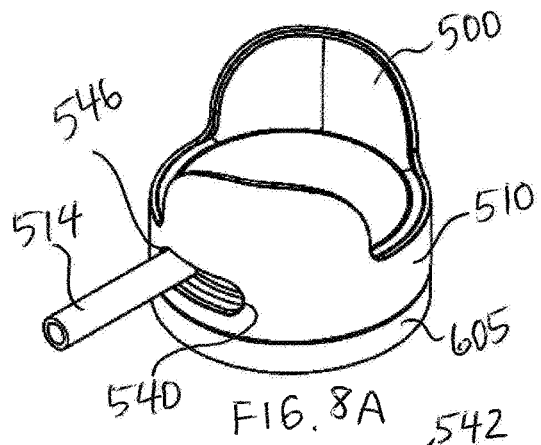
FIGS. 8A-8C show the actuatable assembly interface of FIG. 5 coupled to a locking portion of the actuatable assembly, in the unlocked configuration.
Figure 8B:
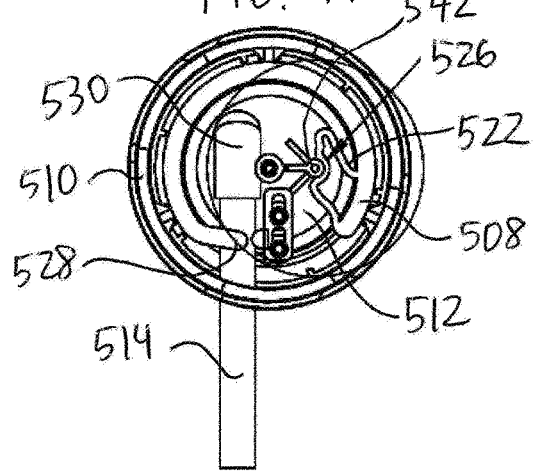
Figure 8C:
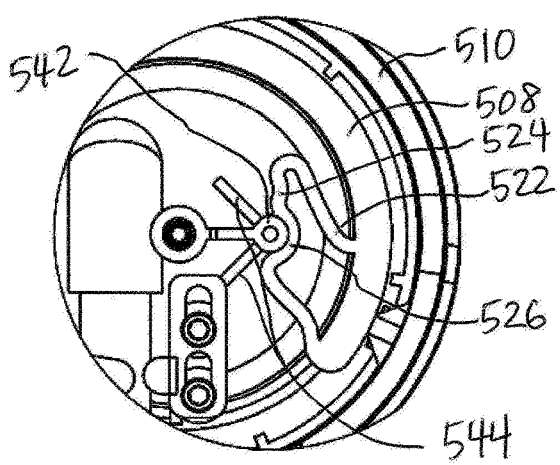

FIGS. 8A-8C show the actuatable assembly interface (AAI) 500 coupled to the locking portion 605 of the actuatable assembly, in the unlocked configuration. FIG. 8A shows an isometric view of the assembly, FIG. 8B shows a top view of the assembly, and FIG. 8C shows a close-up view of a portion of the top view of FIG. 8B. As best seen in FIG. 8B, the tube 514 carrying the driving fluid couples to the base 512, for example via a tube receiving member 530 coupled to or integrally formed with the base. As best seen in FIG. 8A, the external locking ring 510 comprises a cut-out 540 along its side wall, configured to allow passage of the tube 514 therethrough. The cut-out may extend over a sufficient length to allow rotation of the tube within the cut-out while the AAI is locked onto or unlocked from the actuatable assembly. In the unlocked configuration, the tube is disposed adjacent a first end 546 of the cut-out. As best seen in FIG. 8C, the base 512 comprises an engaging element 542, configured to engage either the open detent 524 or the shutoff detent 526 of spring 522 of the internal locking ring 508. When the AAI is not locked onto the actuatable assembly, fluid communication between the breast interface and the AAI is preferably shut off, in order to prevent distension of either the breast interface membrane or the AAI membrane as described herein. Thus, in the unlocked configuration of FIGS. 8A-8C, the engaging element 542 is held in the shutoff detent 526, and correspondingly, the end 528 of the internal locking ring 508 pinches the tube 514 to shut off the fluid communication. The engaging element may be supported by one or more supporting elements 544 to help prevent bending or breakage of the engaging element in response to the forces applied to the engaging element by the spring 522 as the locking ring assembly is rotated with respect to the base.

Figure 9A:
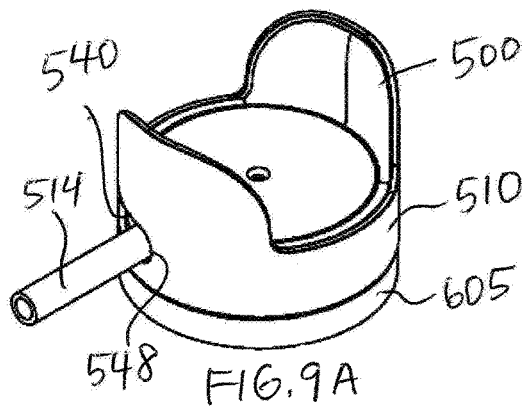
FIGS. 9A-9C show the actuatable assembly interface of FIG. 5 coupled to a locking portion of the actuatable assembly, in the locked configuration.
Figure 9B:
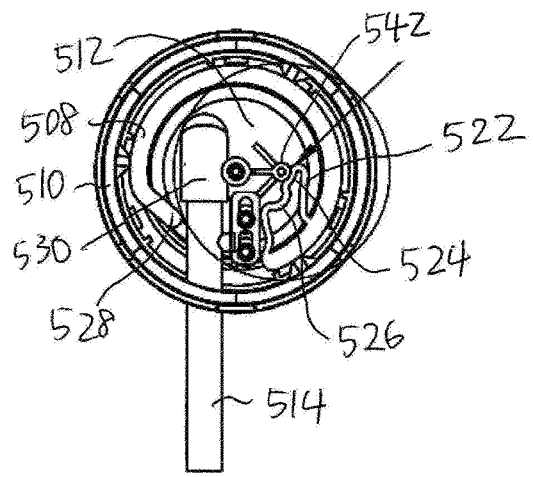
Figure 9C:
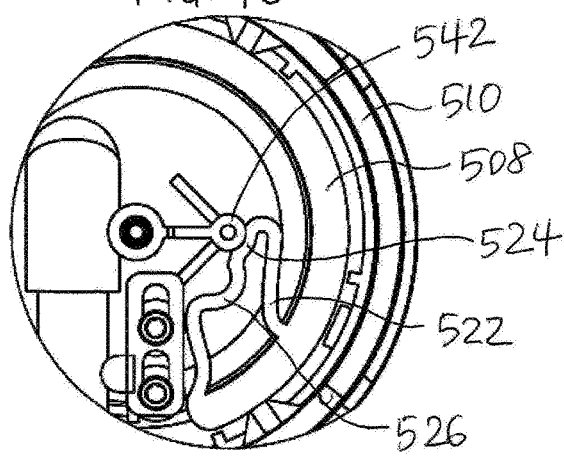

FIGS. 9A-9C show the actuatable assembly interface (AAI) 500 coupled to the locking portion 605 of the actuatable assembly, in the locked configuration. FIG. 9A shows an isometric view of the assembly, FIG. 9B shows a top view of the assembly, and FIG. 9C shows a close-up view of a portion of the top view of FIG. 9B. As best seen in FIG. 9A, in the locked configuration, the tube 514 passing through the cut-out 540 of the external locking ring 510 is disposed adjacent a second end 548 of the cut-out opposite the first end 546 as shown in FIG. 8A. When the AAI is locked onto the actuatable assembly, fluid communication between the breast interface and the AAI can be re-opened, in order to allow the transfer of pressure from the actuatable assembly to the breast interface. Thus, in the locked configuration of FIGS. 9A-9C, the engaging element 542 of the base 512 is held in the open detent 524, and correspondingly, the end 528 of the internal locking ring 508 is decoupled from the tube 514, to allow fluid communication to resume between the AAI and the breast interface.

FIGS. 10A-10B illustrate the locking of the actuatable assembly interface (AAI) 500 onto a locking portion 605 of an actuatable assembly. As described herein, the AAI 500 comprises a locking ring assembly rotatably coupled to a base-cover assembly, wherein the locking ring assembly comprises an external locking ring 510 configured to rotate over the external bearing surface of the base 512. The external locking ring is rotationally coupled with the internal locking ring disposed within the base-cover-assembly, such that rotation of the external locking ring with respect to the base can re-open or shut off fluid communication between the AAI and the breast interface, as described herein. The locking portion 605 of the actuatable assembly comprises a protruding side wall 610 configured to fit within the space 554 between the external locking ring 510 and the base 512. To operably connect the AAI to the actuatable assembly, the AAI can be placed over the locking portion 605 with the space 554 aligned with the side wall 610 of the locking portion. The AAI can then be rotated into a locked position, such that the flexible AAI membrane 504, coupled to the bottom of the base 512, becomes fluidly sealed against the AAI receiving surface 615 of the locking portion 605, and the AAI is securely locked onto the actuatable assembly. The locking of the AAI onto the actuatable assembly can simultaneously re-open fluid communication between the breast interface and the AAI, as described herein.

To facilitate proper rotational alignment of the AAI with respect to the locking portion, each of the external locking ring 510 and base 512 may comprise mechanisms to align and/or lock the AAI onto the locking portion of the actuatable assembly. The base 512 may comprise one or more base aligning features 556, such as one or more rib slots disposed on an external surface of the base side wall and extending through the bottom edge of the side wall. The protruding side wall 610 of the locking portion 605 may comprise one or more base aligning members 620 configured to couple to the base aligning features 556, such as one or more ribs disposed on an internal surface of the side wall 610 configured to fit within the one or more rib slots of the base. The external locking ring 510 may comprise one or more key members 550, such as one or more cam pins disposed on an internal surface of the locking ring side wall, protruding radially inwards. The side wall 610 of the locking portion 605 may comprise one or more lock members 625 corresponding to the one or more key members 550. For example, the one or more lock members may comprise one or more cam paths configured to receive one or more cam pins of the external locking ring therein. The cam paths may be slots or grooves disposed along the external surface of the protruding side wall 610, wherein a cam path may comprise an entry region 626, a ramped region 627, and a locking region 628. The entry region 626 can extend through the top edge of the side wall to provide an entry path for the cam pin of the external locking ring as the AAI is initially lowered into the coupling portion. The ramped region 627 can provide a translational path for the cam pin that slopes slightly downwards. The locking region 628 can lock the AAI into position such that the AAI can resist the vertical thrusting force during actuation of the actuatable assembly.

To couple the AAI 500 to an actuatable assembly as shown in FIGS. 10A-10B, one or more cam pins 550 of the external locking ring 510 can be aligned with the entry regions 626 of one or more corresponding cam paths 625 of the locking portion 605, while one or more rib slots 556 of the base 512 can be aligned with one or more corresponding ribs 620 of the locking portion. Next, the external locking ring may be rotated in the direction 650, such that the cam pin rotatingly translates within the ramped region 627 of the cam path towards the locking region 628. As the AAI is rotated, translation of the cam pin along the downward-sloping ramped region brings the flexible AAI membrane 504 closer to the AAI receiving surface 615 of the coupling portion 605. Eventually, the AAI membrane 504 is compressed against the AAI receiving surface such that the membrane becomes fluidly sealed against the AAI receiving surface. The AAI is rotated until the cam pin reaches and becomes securely held within the locking region of the cam path.

When the AAI is initially lowered onto the locking portion of the actuatable assembly, with the cam pin aligned with the entry region of the cam path, the engaging element 542 of the base 512 is held within the shutoff detent 526 of the internal locking ring 508, as shown in FIG. 8C. In this configuration, the end 528 of the internal locking ring is compressed against the tube 514 carrying the driving fluid, such that fluid communication between the breast interface and the AAI is shut off. As the external locking ring is rotated against the actuatable assembly to translate the cam pin from the entry region to the locking region, sufficient rotational force is exerted to overcome the resistance of the material spring 522 as the engaging element is held within the shutoff detent, and the internal locking ring rotates such that open detent 524 engages the engaging element, as shown in FIG. 9C. Thus, as the AAI is operably coupled with and securely locked onto the actuatable assembly, the fluid communication between the AAI and the breast interface is simultaneously re-opened.

To unlock the AAI from the actuatable assembly, the AAI can be rotated in a direction opposite the direction 650 as shown in FIG. 10B, such that the cam translates along the cam path from the locking region to the entry region, and the AAI membrane is decoupled from the AAI receiving surface of the locking portion. This rotational unlocking movement simultaneously causes the internal locking ring to rotate with sufficient force to deflect the material spring and cause the shutoff detent to re-engage the engaging element. Engagement of the engaging element in the shutoff detent causes the internal locking ring end to fully compress against and pinch off the tube carrying the driving fluid, thereby shutting off the fluid communication between the breast interface and the AAI. The AAI can then be removed from the actuatable assembly by lifting the AAI upwards, with the cam pin translating along the entry region of the cam path.

FIG. 11 is a cross-sectional view of a flexible AAI membrane 504 suitable for incorporation with a hydraulic pumping system as disclosed herein. The AAI membrane 504 may comprise an annular lip 560 configured to engage a corresponding annular groove formed in the base, to securely couple to the AAI membrane to the base. The AAI membrane may further comprise a sealing flap or flange 558 disposed at its proximal end facing the actuatable assembly, and extending annularly about the periphery of the membrane. The sealing flap may extend proximally beyond the bottom surface of the base, such that the sealing flap engages the AAI receiving surface of the locking portion of the actuatable assembly when the AAI is coupled to the locking portion of the actuatable assembly. The sealing flap may be configured to deform on contact to allow at least a portion of the air trapped between the AAI membrane the AAI receiving surface to escape, but not easily re-enter. The sealing flap can thus facilitate the formation of a fluid seal between the AAI and the actuatable assembly. Various design parameters of the sealing flap may be modified such that the sealing flap can form a complete fluid seal against the actuatable assembly when the actuatable assembly is actuated. For example, the thickness and/or geometry of the flap may be modified, or the height at which the sealing flap is seated against the AAI receiving surface when the AAI is locked onto the actuatable assembly may be modified, such that the sealing flap can allow substantially all of the air trapped between the AAI and the actuatable assembly to escape the space when the actuatable assembly is actuated.

A thus-configured sealing flap may eliminate the need for a separate one-way valve coupled to either the actuatable assembly or the AAI to allow air trapped between the two parts to be pushed out, such as the one-way valve 393 shown and described with reference to FIG. 3B.

Figure 12A:
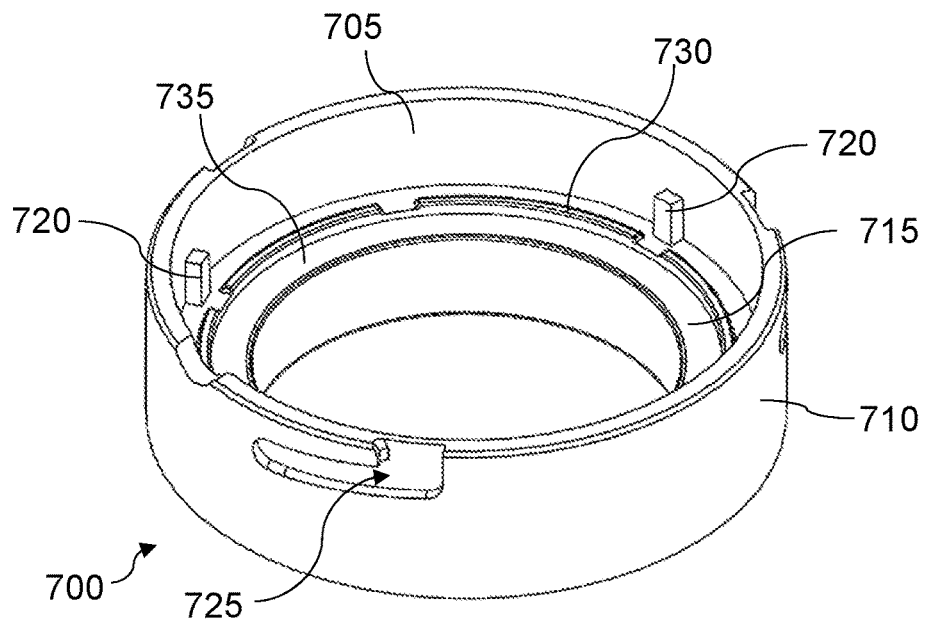
FIG. 12A shows an exemplary configuration of an actuatable assembly in accordance with embodiments.
Figure 12B:
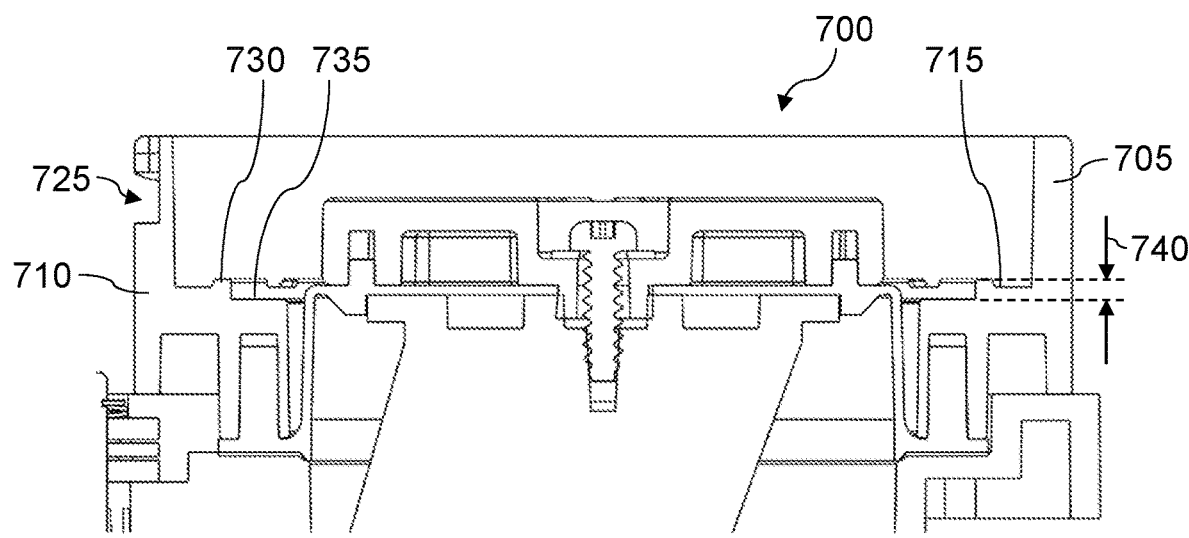
FIG. 12B is a side cross-sectional view of an actuatable assembly in accordance with embodiments.

FIGS. 12A-12B illustrate an exemplary configuration of an actuatable assembly suitable for incorporation with a hydraulic pumping system as disclosed herein. FIG. 12A is an isometric view of a locking portion 705 of actuatable assembly 700. FIG. 12B is a side cross-sectional view of a portion of actuatable assembly 700 including the locking portion 705. Actuatable assembly 700 may comprise a locking portion 705 configured to couple to an actuatable assembly interface of a breast shield assembly as described herein. Locking portion 705 may be similar in many aspects to locking portion 605 as shown in and described in reference to FIGS. 5-10B. For example, the locking portion 705 may comprise an AAI receiving surface 715, one or more base aligning members 720, and/or one or more lock members 725 such as one or more cam paths formed in the side wall 710.

AAI receiving surface 715 may comprise a sealing surface 735 configured to seal against the sealing flap or flange of the AAI membrane as described herein. The AAI receiving surface may further comprise an annular rib 730, which may be disposed about the outer periphery of the sealing surface 735. The annular rib 730 may be a single, continuous rib, or it may comprise a plurality of portions arranged annularly, as best shown in FIG. 12A. The annular rib may have a vertical offset 740 with respect to the sealing surface 735, as best shown in FIG. 12B. The vertical offset may be calibrated to allow movement of the sealing flap of the AAI membrane when the AAI is coupled to the actuatable assembly, as described in further detail with reference to FIG. 13.

Figure 13:
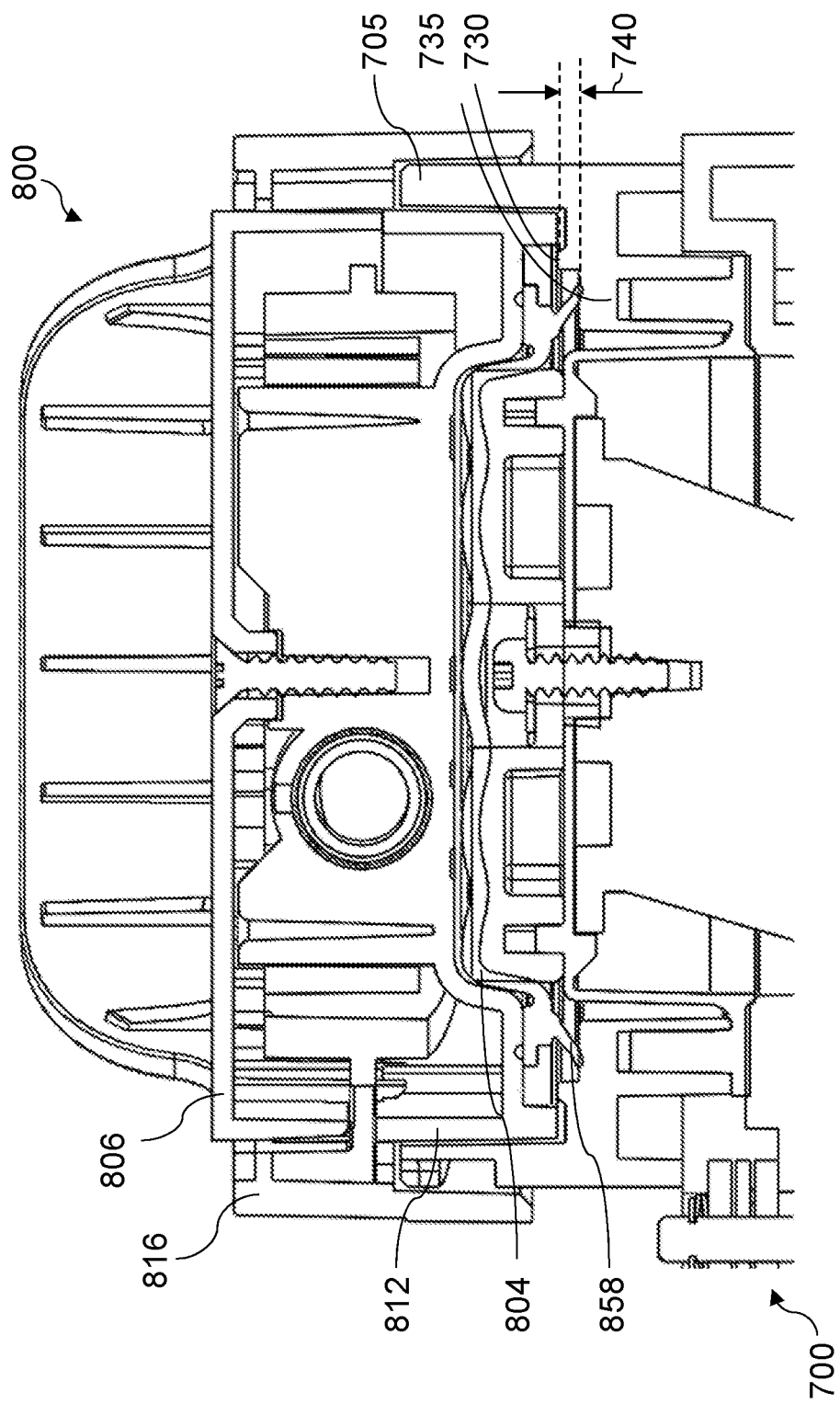
FIG. 13 is a side cross-sectional view of the actuatable assembly of FIGS. 12A and 12B coupled to an actuatable assembly interface in accordance with embodiments.

FIG. 13 is a side cross-sectional view of the actuatable assembly of FIGS. 12A and 12B coupled to an actuatable assembly interface (AAI) as disclosed herein. AAI 800 may be similar in many aspects to the AAI 500 shown in and described with reference to FIGS. 5-11. For example, AAI 800 may comprise a cover 806, base 812, and locking ring 816 coupled together to form the housing, wherein the base may be coupled to an AAI membrane 804. AAI membrane 804 may comprise a sealing flap 858 configured to form a fluid seal against an AAI receiving surface of the actuatable assembly. AAI 800 may be configured to removably couple to the locking portion 705 of the actuatable assembly 700 via one or more of many mechanisms described herein with reference to various embodiments. As described with reference to FIGS. 12A and 12B, the locking portion 705 may comprise an AAI receiving surface defining a sealing surface 735 and an annular rib 730, the annular rib having a vertical offset 740 with respect to the sealing surface. The annular rib 730 may be disposed about the outer periphery of the sealing surface 735, such that when the AAI is coupled to the actuatable assembly, the annular rib comes into contact with the bottom surface of the AAI base 812 disposed about the outer periphery of the sealing flap 858, without contacting the sealing flap 858. The vertical offset 740 may be calibrated to allow sufficient movement of the sealing flap to allow the sealing flap to function as an air outlet valve when the AAI is lockingly coupled to the actuatable assembly. Such a configuration can allow the AAI membrane sealing flap to function as a one-way valve to expel excess air trapped between the AAI and the actuatable assembly, thus eliminating the need for a separate one-way valve such as one-way valve 395 shown in and described with reference to FIG. 3B.

While FIGS. 12A-13 illustrate the actuatable assembly comprising a feature to adjust the height at which the AAI membrane sealing flap is seated against the AAI receiving surface when the AAI is locked onto the actuatable assembly, such a feature may be added to the AAI instead. For example, the bottom surface of the AAI base may comprise an annular rib disposed about the outer periphery of the sealing flap, wherein the annular rib may be configured to contact the AAI receiving surface when the AAI is coupled to the actuatable assembly. The annular rib may have a height configured to set the sealing flap at a distance from the AAI receiving surface predetermined to allow sufficient movement of the sealing flap for expelling trapped air between the AAI and the actuatable assembly.

FIGS. 14A-14D illustrate exemplary configurations of an actuatable assembly interface (AAI) 900 suitable for incorporation with a hydraulic pumping system as disclosed herein. AAI 900 may be configured with a mechanism that enables reversible shut-off of fluid communication between the breast interface and the AAI, as described herein. AAI 900 may be similar in many aspects to AAI 500 shown in and described with reference to FIGS. 5-11. For example, AAI 900 may comprise a housing coupled to an AAI membrane and a tube containing the driving fluid for the breast shield assembly. The AAI housing may comprise a cover, a locking ring 916, and a base 912, which may be similar in many aspects to cover 506, locking ring assembly 516, and base 512, respectively, as shown and described with reference to FIGS. 5-11.

Figure 14A:
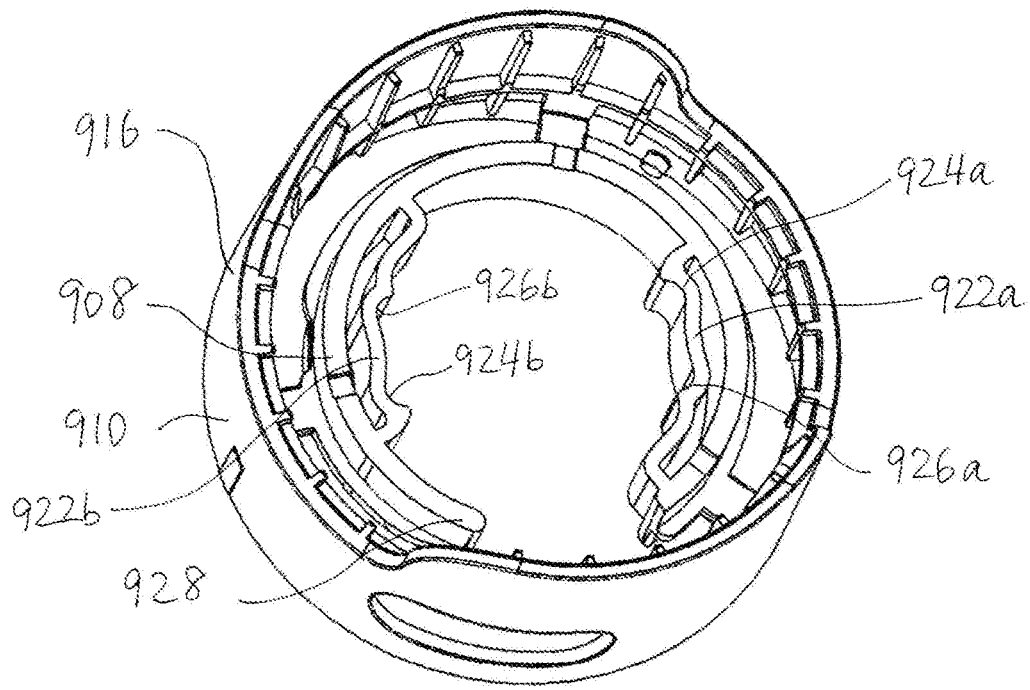
FIG. 14A shows an exemplary configuration of a locking ring of an actuatable assembly interface in accordance with embodiments.

FIG. 14A shows an exemplary configuration of a locking ring 916 of AAI 900. Locking ring 916 may comprise an internal ring portion 908 and an external ring portion 910, which may be similar in many aspects to the internal locking ring 508 and external locking ring 510, respectively, as described elsewhere herein. The internal and external ring portions may be fixedly coupled together at a predetermined orientation as shown, such that the two portions are rotationally fixed relative to one another. The internal ring portion 908 may comprise a partial ring having two ends, wherein one end may comprise a tip 928 configured to push against the tube carrying the driving fluid when AAI 900 is detached from the actuatable assembly, as described in further detail with reference to FIGS. 14C-14D. The internal ring portion 908 may further comprise two springs 922a and 922b, collectively configured to hold the AAI in the locked or the unlocked configuration. The springs 922a and 922b may be material springs integrally formed with the internal ring portion, as shown in FIG. 14A, or they may comprise separate components such as ball plungers or leaf fingers. The springs 922a and 922b may be similar in many aspects to spring 522 described with reference to FIGS. 6A-6B. For example, each spring may comprise a detent geometry configured to engage corresponding engaging elements of the AAI base 912. The detent geometry may define an open detent 924a, 924b and a shutoff detent 926a, 926b, wherein the open detents may be configured to engage the engaging elements when the AAI is locked onto the actuatable assembly, and wherein the shutoff detents may be configured to engage the engaging elements when the AAI is not locked onto the actuatable assembly. The open and shutoff detents may configured such that a greater amount of force is required for an engaging element to move from the shutoff detent to the open detent than to move from the open detent to the shutoff detent, thereby ensuring that fluid communication between the breast interface and the AAI remains securely shut off while the AAI is not coupled to the actuatable assembly. The two springs 922a and 922b may be arranged symmetrically about the locking ring, such that the forces applied to the springs by the corresponding engaging elements of the base 912 are distributed evenly about the locking ring. The rotational distribution of forces can improve the structural robustness of the AAI, especially when the AAI is in the unlocked configuration and torque is exerted onto components of the AAI due to the tendency of the pinched tube to resume its natural (open) shape.

Figure 14B:
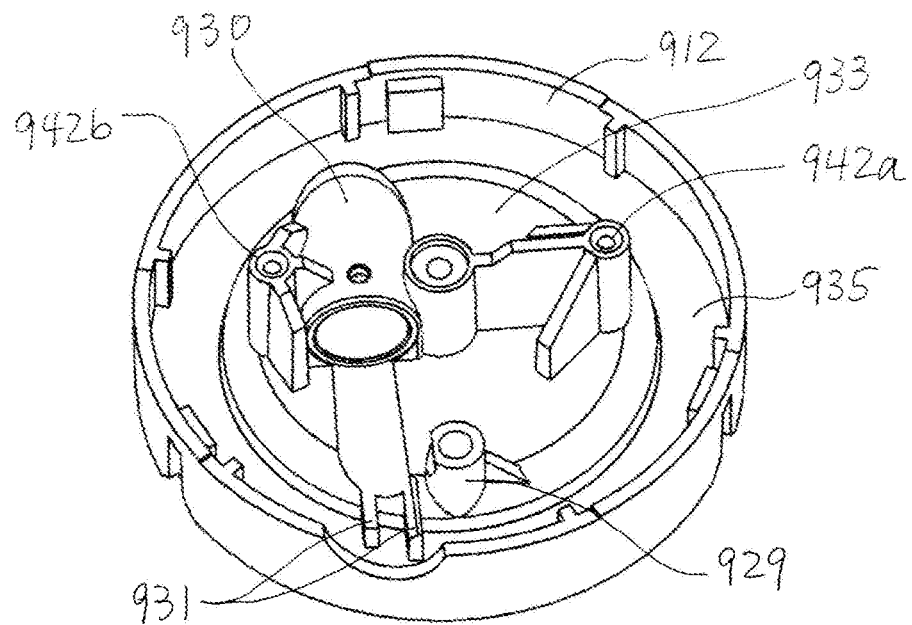
FIG. 14B shows an exemplary configuration of an actuatable assembly interface base in accordance with embodiments.

FIG. 14B shows an exemplary configuration of a base 912 of AAI 900. Base 912 may comprise two engaging elements 942a and 942b, which may be integrally formed with the base material. The engaging elements 942a and 942b may be configured to engage the springs 922a and 922b, respectively, of the locking ring 916, when AAI 900 is assembled. Base 912 may further comprise a tube receiving member 930 configured to couple to the tube carrying the driving fluid. For example, as shown in FIG. 14B, the tube receiving member may comprise a bore having an inner diameter sized to receive the tube therein, wherein the bore is in fluid communication with the space between the AAI base and the AAI membrane coupled to the bottom surface of the AAI base. The tube receiving member 930 may be disposed on a central portion 933 of the base bottom, wherein the central portion 933 may be slightly raised relative to the peripheral portion 935 of the base bottom extending about the periphery of the central portion. The AAI membrane may be coupled to the base at the peripheral portion 935 (e.g., via an annular lip 560 as shown in FIG. 11, configured to fit within a corresponding annular groove of the peripheral portion 935), such that a cavity or fluid reservoir is formed between the central portion 933 of the base bottom and the AAI membrane. In use, this cavity may be filled with the driving fluid for the hydraulic pumping system (e.g., water or other substantially incompressible fluid), so as to fluidly couple the AAI membrane to the breast interface membrane. Base 912 may further comprise a tube pinching member 929 configured to support the tube when the tube is pushed by the tip 928 of the locking ring, thereby pinching the tube shut between the pinching member 929 and tip 928. Base 912 may further comprise one or more tube supporting members 931 configured to be disposed underneath the tube when the tube is attached to the base. The supporting members 931 may extend from the raised central portion 933 at least partially over the peripheral portion 935, to prevent the tube from sliding below the level of the locking ring tip 928 and pinching member 929 when the tube is captured between the tip 928 and pinching member 92, thereby ensuring that the tube is pinched off completely when the AAI is in the shutoff configuration.

Figure 14C:
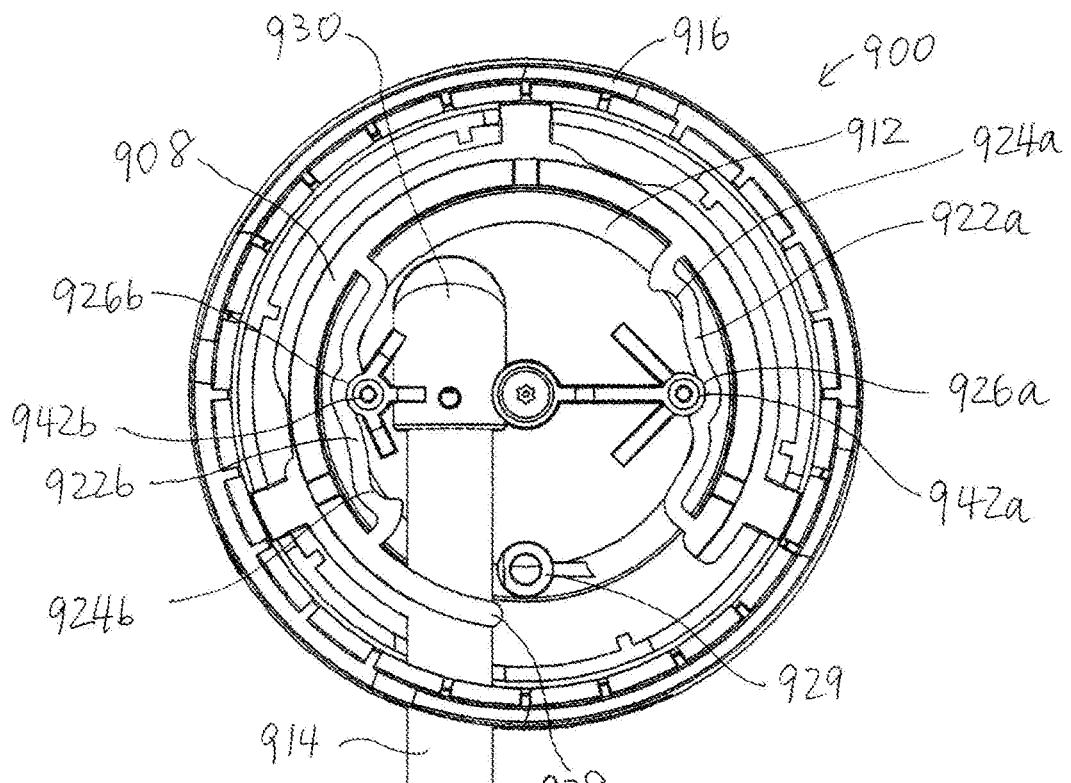
FIG. 14C is a top view of an exemplary actuatable assembly interface in the unlocked configuration.

FIG. 14C is a top view of AAI 900 in the unlocked configuration, wherein the AAI is not attached to the actuatable assembly and fluid communication between the AAI and the breast interface is shut off. In the unlocked configuration, the engaging elements 942a and 942b of the base 912 are held within the shutoff detents 926a and 926b of the springs 922a and 922b, and the tip 928 of the internal ring portion 908 is pushing the tube 914 into the tube pinching member 929, so as to pinch the tube shut. As shown, the radial positions of the tip 928 and pinching member 929 with respect to the center of the base 912 may be slightly offset, so as to reduce the rotational forces exerted onto the springs by the resistance of the tube to being pinched closed, and thereby more securely hold the tube pinched shut.

Figure 14D:
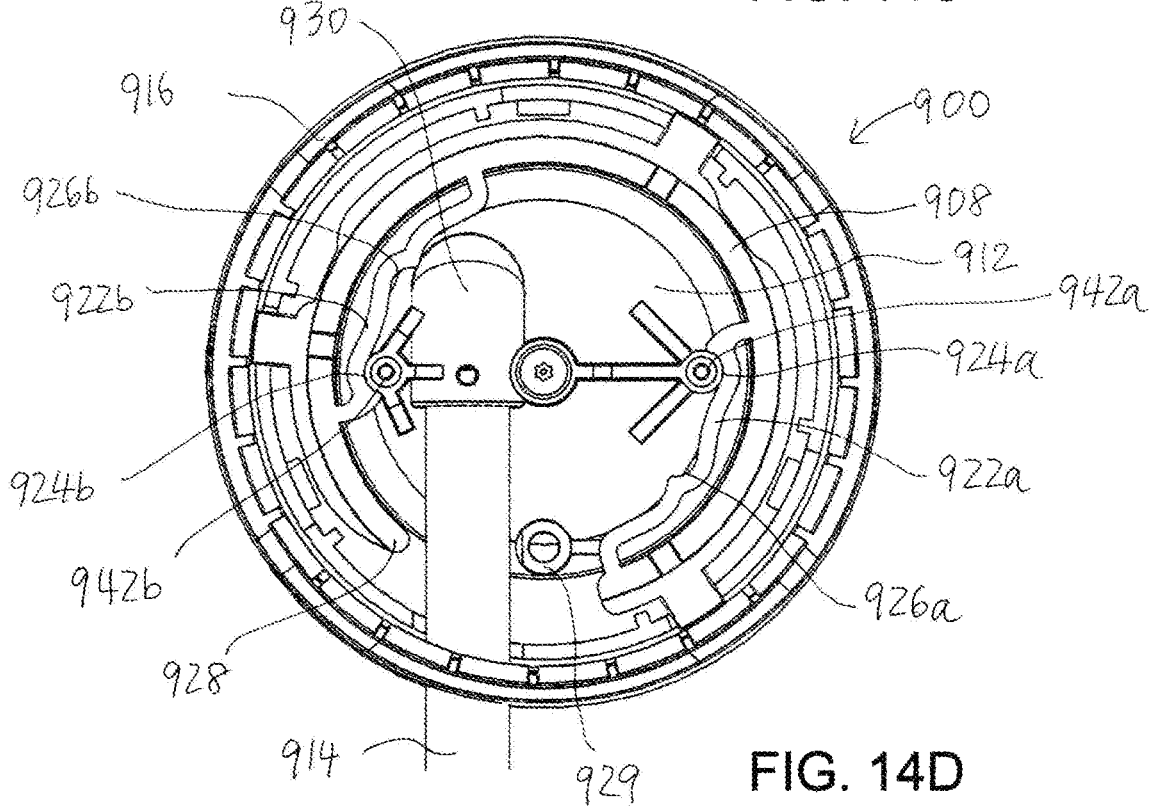
FIG. 14D is a top view of the actuatable assembly interface of FIG. 14C in the locked configuration.

FIG. 14D is a top view of AAI 900 in the locked configuration, wherein the AAI is attached to the actuatable assembly and fluid communication between the AAI and the breast interface is re-opened. In the locked configuration, engaging elements 942a and 942b of the locking ring are held within the open detents 924a and 924b, and tip 928 of the internal ring portion 908 is not pushing into the tube 914 to any extent that substantially obstructs fluid passage through the tube.

FIGS. 15A-15C illustrate an exemplary configuration of an AAI base 1012 suitable for incorporation with a hydraulic pumping system as disclosed herein. FIG. 15A shows a barbed adaptor 1013 suitable for incorporation with an AAI as described herein. FIG. 15B shows the barbed adaptor 1013 of FIG. 15A coupled to an AAI base 1012. FIG. 15C is a side cross-sectional view of the AAI base 1012 with the barbed adaptor 1013 as shown in FIG. 15B. AAI base 1012 may comprise a barbed adaptor 1013, configured to securely couple the tube carrying the driving fluid to the base 1012. The barbed adaptor 1013 may comprise one or more barbed regions 1015 configured to couple to the tubing, and an insertion region 1017 configured to insert into the bore of the tube receiving member 1030 of the base. The barbed region 1015 may be shaped and dimensioned to ensure that the tube is fluidly sealed against the adaptor when the tube is disposed over the barbed region. The insertion region 1017 may comprise one or more o-ring grooves 1019 configured to receive one or more o-rings 1021 therein, to ensure that the adaptor is fluidly sealed against the bore of the tube receiving member. The barbed adaptor 1013 can thereby help ensure that the joint between the tube and the AAI base is fluidly sealed. To further secure the coupling between the adaptor and the tube receiving member, the adaptor may be glued into the bore of the tube receiving member. To facilitate the gluing of the adaptor to the bore, the tube receiving member may comprise a glue potting hole 1031, and the adaptor may comprise a glue potting groove 1023 configured to align with the hole 1031 when the adaptor is inserted into the bore of the tube receiving member. Other aspects of the AAI base 1012 may be similar to various embodiments of an AAI base as described herein.

While FIGS. 15A-15C show an AAI base comprising a separate barbed adaptor that is coupled to the base, in some embodiments, a barbed fitting for the tubing may be integrally formed with the base. For example, the tube receiving member may comprise a barbed fitting with a bore in fluid communication with the cavity formed between the AAI base and the AAI membrane.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus for expression of breast milk from a breast, the apparatus comprising:
   a breast interface configured to receive and fluidly seal against the breast, the breast interface comprising a first fluid reservoir;

an actuatable assembly interface configured to removably couple to an actuatable assembly, the actuatable assembly interface comprising a second fluid reservoir; and a tube having a first end coupled to the breast interface and a second end coupled to the actuatable assembly interface, such that the first fluid reservoir and the second fluid reservoir are in fluid communication, wherein the first fluid reservoir, the second fluid reservoir, and the tube are filled with a driving fluid, and wherein the actuatable assembly interface comprises a fluid shutoff mechanism to reversibly shut off fluid communication between the first fluid reservoir and the second fluid reservoir;

wherein the fluid shutoff mechanism is configured to shut off fluid communication between the first and second fluid reservoirs in response to detachment of the actuatable assembly interface from the actuatable assembly, and re-open the fluid communication in response to attachment of the actuatable assembly interface to the actuatable assembly;

wherein the fluid shutoff mechanism is configured to simultaneously secure coupling of the actuatable assembly interface to the actuatable assembly and release pinching of the tube to open the tube, and to simultaneously release coupling of the actuatable assembly interface to the actuatable assembly and pinch the tube closed;

wherein the fluid shutoff mechanism comprises one or more springs and one or more engaging members configured to engage the one or more springs in a first configuration when the actuatable assembly interface is detached from the actuatable assembly, or in a second configuration different from the first configuration when the actuatable assembly interface is attached to the actuatable assembly;

wherein the one or more springs comprises one or more material springs each having a detent geometry, the detent geometry defining a first detent and a second detent configured to engage the one or more engaging members in the first configuration or in the second configuration, respectively.

2. An apparatus as in claim 1, wherein the driving fluid has a density that is higher than the density of air.

3. An apparatus as in claim 1, wherein the driving fluid is substantially incompressible.

4. An apparatus as in claim 1, wherein the breast interface comprises a first housing and a distal membrane coupled thereto to form the first fluid reservoir therebetween, wherein the actuatable assembly interface comprises a second housing and a proximal membrane coupled thereto to form the second fluid reservoir therebetween, and wherein the distal and proximal membranes are flexible to allow movement of the driving fluid into or out of the first and second fluid reservoirs.

5. An apparatus as in claim 4, wherein the proximal membrane is configured to seal against an actuatable assembly membrane when the actuatable assembly interface is coupled to the actuatable assembly, wherein the actuatable assembly membrane is coupled with a driver mechanism of the actuatable assembly, such that movement of the actuatable assembly membrane in response to actuation of the driver mechanism causes corresponding movement of the proximal membrane.

6. An apparatus as in claim 5, wherein the proximal membrane comprises a sealing flap configured to allow air trapped between the proximal membrane and the actuatable assembly membrane to exit.

7. An apparatus as in claim 4, wherein the second housing of the actuatable assembly interface comprises a tube receiving member configured to couple to the second end of the tube, the tube receiving member defining a bore that is in fluid communication with the second fluid reservoir through an opening in the second housing.

8. An apparatus as in claim 5, wherein the tube receiving member comprises a barbed region configured to receive the tube thereover and form a fluid seal thereagainst.

9. An apparatus as in claim 5, wherein the actuatable assembly interface further comprises a barbed adaptor configured to fit within and fluidly seal against the bore of the tube receiving member, the barbed adaptor comprising a barbed region configured to receive the tube thereover and form a fluid seal thereagainst.

10. An apparatus as in claim 1, wherein the fluid shutoff mechanism is configured to secure or release the coupling of the actuatable assembly interface to the actuatable assembly and simultaneously release or pinch the tube via rotational movement of the actuatable assembly interface with respect to the actuatable assembly.

11. An apparatus as in claim 1, wherein the one or more springs are configured such that a greater force is required to disengage the one or more engaging members from the one or more springs in the first configuration than in the second configuration.

12. An apparatus as in claim 1, wherein the fluid shutoff mechanism is configured to secure or release the coupling of the actuatable assembly interface to the actuatable assembly and simultaneously release or pinch the tube via rotational movement of the actuatable assembly interface with respect to the actuatable assembly, and wherein the one or more springs and one or more engaging members comprise a plurality of springs.

13. An apparatus as in claim 12, wherein the plurality of springs and the plurality of engaging members are distributed in a rotationally symmetric manner about the actuatable assembly interface.

14. An apparatus as in claim 1, wherein the actuatable assembly interface comprises a keyed locking mechanism configured to allow attachment and removal of the actuatable assembly interface to and from the actuatable assembly only when the fluid communication between the first and second fluid reservoirs is shut off.

15. A system for expression of breast milk from a breast, the system comprising:
an actuatable assembly comprising a driver mechanism coupled to an actuatable assembly membrane; and
an actuatable assembly interface configured to removably couple to the actuatable assembly, the actuatable assembly interface comprising a housing and a flexible membrane coupled together to form a second fluid reservoir therebetween,
wherein the second fluid reservoir of the actuatable assembly interface is in fluid communication with a first fluid reservoir of a breast interface via a tube, and
wherein the housing comprises a fluid shutoff mechanism to reversibly shut off fluid communication between the first and second fluid reservoirs;
wherein the flexible membrane is configured to seal against the actuatable assembly membrane when the actuatable assembly interface is coupled to the actuatable assembly, such that movement of the actuatable assembly membrane in response to actuation of the driver mechanism causes corresponding movement of the flexible membrane;

wherein the flexible membrane comprises a sealing flap configured to expel air trapped between the flexible membrane and the actuatable assembly membrane when the driver mechanism moves the actuatable assembly membrane towards the flexible membrane;

wherein the actuatable assembly comprises a receiving surface configured to receive the actuatable assembly interface, the receiving surface defining an sealing surface configured to seal against the sealing flap and an annular rib disposed about the outer periphery of the sealing surface, wherein the annular rib is vertically offset from the sealing surface by a height predetermined to allow sufficient movement of the sealing flap to expel the air trapped between the flexible membrane and the actuatable assembly membrane.

* * * * *